(12) United States Patent
Augustine et al.

(10) Patent No.: US 10,575,784 B2
(45) Date of Patent: Mar. 3, 2020

(54) PATIENT SECURING OVERLAY FOR HEATED UNDERBODY SUPPORTS

(71) Applicant: Augustine Temperature Management LLC, Eden Prairie, MN (US)

(72) Inventors: Scott D. Augustine, Deephaven, MN (US); Randall C. Arnold, Minnetonka, MN (US); Scott A. Entenman, St. Paul, MN (US); Rudolf Andreas Deibel, Eden Prairie, MN (US); Brent M. Augustine, Minneapolis, MN (US); Garrett J. Augustine, Deephaven, MN (US); Ryan S. Augustine, Saint Louis Park, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 0 days.

(21) Appl. No.: 16/209,020

(22) Filed: Dec. 4, 2018

(65) Prior Publication Data
US 2019/0104996 A1 Apr. 11, 2019

Related U.S. Application Data

(63) Continuation of application No. 15/918,311, filed on Mar. 12, 2018, which is a continuation of application
(Continued)

(51) Int. Cl.
*A47C 21/00* (2006.01)
*A61B 5/00* (2006.01)
(Continued)

(52) U.S. Cl.
CPC .......... *A61B 5/6892* (2013.01); *A47C 21/048* (2013.01); *A47C 27/081* (2013.01);
(Continued)

(58) Field of Classification Search
CPC ................................ A47C 21/00; A47C 21/04
(Continued)

(56) References Cited

U.S. PATENT DOCUMENTS 2,403,676 A 7/1946 Modlinski
2,497,186 A 2/1950 Pedersen
(Continued)

FOREIGN PATENT DOCUMENTS

DE 3343664 C1 3/1985
DE 10065592 A1 7/2002
(Continued)

OTHER PUBLICATIONS

Eeon TexTM Conductive Testiles, Product Details, www.eeonyx.com/prodte.html, Sep. 19, 2006, pp. 1-5.
(Continued)

*Primary Examiner* — Fredrick C Conley
(74) *Attorney, Agent, or Firm* — Fredrikson & Byron, P.A.

(57) ABSTRACT

Apparatus and methods related to an underbody support for supporting a body of a being, such as during surgery to prevent contact pressure injuries. In certain embodiments, the underbody support may include one or more inflatable chambers enclosing a volume. At least one of the inflatable chambers may include one or more compression sensitive switches for monitoring the volume of the inflatable chamber, and the one or more compression sensitive switches may be located within the inflatable chamber. In some embodiments the one or more compression sensitive switches are sized to close when the said inflatable chamber is deflated to a desired residual volume.

22 Claims, 17 Drawing Sheets

Related U.S. Application Data

No. 14/683,825, filed on Apr. 10, 2015, now Pat. No. 9,962,122, application No. 16/209,020, which is a continuation of application No. 14/683,915, filed on Apr. 10, 2015.

(60) Provisional application No. 61/977,930, filed on Apr. 10, 2014.

(51) Int. Cl.

| | |
|---|---|
| *A47C 21/04* | (2006.01) |
| *H05B 3/36* | (2006.01) |
| *A61G 7/057* | (2006.01) |
| *A61B 5/01* | (2006.01) |
| *A61B 18/16* | (2006.01) |
| *A61F 7/00* | (2006.01) |
| *A61F 7/08* | (2006.01) |
| *A47C 27/08* | (2006.01) |
| *A47C 27/10* | (2006.01) |
| *A61G 7/005* | (2006.01) |
| *A61G 7/05* | (2006.01) |
| *A61G 13/12* | (2006.01) |
| *A61B 5/11* | (2006.01) |

(52) U.S. Cl.
CPC ............... *A47C 27/10* (2013.01); *A61B 5/01* (2013.01); *A61B 18/16* (2013.01); *A61F 7/007* (2013.01); *A61F 7/08* (2013.01); *A61G 7/005* (2013.01); *A61G 7/05* (2013.01); *A61G 7/05769* (2013.01); *A61G 13/12* (2013.01); *A61G 13/1265* (2013.01); *H05B 3/36* (2013.01); *A61B 5/1116* (2013.01); *A61B 2562/0247* (2013.01); *A61B 2562/043* (2013.01); *A61B 2562/18* (2013.01); *A61B 2562/24* (2013.01); *A61F 2007/0071* (2013.01); *A61F 2007/0091* (2013.01); *A61F 2007/0096* (2013.01); *A61G 2203/34* (2013.01); *A61G 2203/40* (2013.01); *A61G 2203/46* (2013.01); *A61G 2210/50* (2013.01); *A61G 2210/90* (2013.01)

(58) Field of Classification Search
USPC ............... 5/706, 710, 713, 421, 423, 652.2
See application file for complete search history.

(56) References Cited

U.S. PATENT DOCUMENTS

| | | |
|---|---|---|
| 2,706,768 A | 4/1955 | Kaplan |
| 2,715,674 A | 8/1955 | Abbott et al. |
| 2,873,352 A | 2/1959 | Franco |
| 3,008,152 A | 11/1961 | Seidenberg |
| 3,134,891 A | 5/1964 | Hyer |
| 3,137,871 A | 6/1964 | Florio |
| 3,340,549 A | 9/1967 | Billerbeck |
| 3,380,087 A | 4/1968 | Petty et al. |
| 3,582,456 A | 6/1971 | Stolki |
| 3,634,655 A | 1/1972 | Jordan |
| 3,690,325 A | 9/1972 | Kenny |
| 3,780,262 A | 12/1973 | Rudd |
| 3,808,403 A | 4/1974 | Gunma et al. |
| 3,839,621 A | 10/1974 | Hariu |
| 3,854,156 A | 12/1974 | Williams |
| 3,874,504 A | 4/1975 | Veraka |
| 3,900,654 A | 8/1975 | Stinger |
| 3,936,661 A | 2/1976 | Furuishi et al. |
| 4,061,898 A | 12/1977 | Murray et al. |
| 4,118,531 A | 10/1978 | Hauser |
| 4,149,066 A | 4/1979 | Niibe |
| 4,186,294 A | 1/1980 | Bender |
| 4,250,398 A | 2/1981 | De Fonso et al. |
| 4,270,040 A | 5/1981 | McMullan et al. |
| 4,363,947 A | 12/1982 | Bergersen |
| 4,423,308 A | 12/1983 | Callaway et al. |
| 4,479,795 A | 10/1984 | Mustacich et al. |
| 4,495,402 A | 1/1985 | Burdick et al. |
| 4,534,886 A | 8/1985 | Kraus et al. |
| 4,582,564 A | 4/1986 | Shanefield et al. |
| 4,626,664 A | 12/1986 | Grise |
| 4,658,119 A | 4/1987 | Endo et al. |
| 4,660,388 A | 4/1987 | Greene, Jr. |
| 4,661,689 A | 4/1987 | Harrison |
| 4,676,247 A | 6/1987 | Van Cleve |
| 4,682,447 A | 7/1987 | Osborn |
| 4,691,762 A | 9/1987 | Elkins et al. |
| 4,719,335 A | 1/1988 | Batliwalla et al. |
| 4,747,409 A | 5/1988 | Silen |
| 4,764,665 A | 8/1988 | Orban et al. |
| 4,798,936 A | 1/1989 | Johnson |
| 4,899,749 A | 2/1990 | Laroco |
| 4,912,306 A | 3/1990 | Grise et al. |
| 4,930,317 A | 6/1990 | Klein |
| 4,941,961 A | 7/1990 | Noguchi et al. |
| 4,989,283 A | 2/1991 | Krouskop |
| 5,008,515 A | 4/1991 | McCormack |
| 5,010,233 A | 4/1991 | Henschen et al. |
| 5,023,433 A | 6/1991 | Gordon |
| 5,032,705 A | 7/1991 | Batcheller et al. |
| 5,072,598 A | 12/1991 | Dibrell |
| 5,074,285 A | 12/1991 | Wright |
| 5,086,629 A | 2/1992 | Dibrell |
| 5,255,390 A | 10/1993 | Gross et al. |
| 5,320,164 A | 6/1994 | Szczesuil et al. |
| 5,352,870 A | 10/1994 | Daugherty et al. |
| 5,380,580 A | 1/1995 | Rogers et al. |
| 5,383,918 A | 1/1995 | Panetta |
| 5,395,399 A | 3/1995 | Rosenwald |
| 5,422,462 A | 6/1995 | Kishimoto |
| 5,443,056 A | 8/1995 | Smith et al. |
| 5,473,783 A | 12/1995 | Allen |
| 5,496,358 A | 3/1996 | Rosenwald |
| 5,605,144 A | 2/1997 | Simmons et al. |
| 5,638,438 A | 6/1997 | Keen |
| 5,723,845 A | 3/1998 | Partington et al. |
| 5,755,275 A | 5/1998 | Lorney et al. |
| 5,773,275 A | 6/1998 | Anderson et al. |
| 5,815,864 A * | 10/1998 | Sloop ............... A61G 7/05769 5/706 |
| 5,817,145 A | 10/1998 | Augustine et al. |
| 5,824,996 A | 10/1998 | Kochman et al. |
| 5,835,983 A | 11/1998 | McMahen et al. |
| 5,878,620 A * | 3/1999 | Gilbert ............... B60N 2/002 180/273 |
| 5,881,410 A | 3/1999 | Yamada |
| 5,895,973 A | 4/1999 | Fessenden |
| 5,928,274 A | 7/1999 | Augustine |
| 5,932,129 A | 8/1999 | Hyatt |
| 5,948,303 A | 9/1999 | Larson |
| 5,964,792 A | 10/1999 | Augustine |
| 5,970,542 A | 10/1999 | Mays |
| 5,974,605 A | 11/1999 | Dickerhoff et al. |
| 5,986,243 A | 11/1999 | Campf |
| 6,030,412 A | 2/2000 | Klatz et al. |
| 6,038,722 A | 3/2000 | Giori et al. |
| 6,053,910 A | 4/2000 | Fleenor |
| 6,054,331 A | 4/2000 | Woo et al. |
| 6,078,026 A | 6/2000 | West |
| 6,084,217 A | 7/2000 | Bulgajewski |
| 6,093,910 A | 7/2000 | McClintock et al. |
| 6,147,333 A | 11/2000 | Mattson |
| 6,149,674 A | 11/2000 | Borders |
| 6,172,344 B1 | 1/2001 | Gordon et al. |
| 6,180,929 B1 | 1/2001 | Pearce |
| 6,184,496 B1 | 2/2001 | Pearce |
| 6,189,487 B1 | 2/2001 | Owen et al. |
| 6,210,427 B1 | 4/2001 | Augustine et al. |
| 6,214,000 B1 | 4/2001 | Fleenor et al. |
| 6,215,111 B1 | 4/2001 | Rock et al. |
| 6,229,123 B1 | 5/2001 | Kochman et al. |
| 6,229,126 B1 | 5/2001 | Ulrich et al. |

(56) References Cited

U.S. PATENT DOCUMENTS

| | | |
|---|---|---|
| 6,235,049 B1 | 5/2001 | Nazerian |
| 6,240,623 B1 | 6/2001 | Johansson |
| 6,348,678 B1 | 2/2002 | Loyd et al. |
| 6,373,034 B1 | 4/2002 | Rock et al. |
| 6,403,935 B2 | 6/2002 | Kochman et al. |
| 6,416,534 B1 | 7/2002 | Montagnino et al. |
| 6,434,328 B2 | 8/2002 | Rutherford |
| 6,452,138 B1 | 9/2002 | Kochman et al. |
| 6,452,139 B1 | 9/2002 | Benoit et al. |
| 6,483,087 B2 | 11/2002 | Gardner et al. |
| 6,493,889 B2 | 12/2002 | Kocurek |
| 6,544,258 B2 | 4/2003 | Fleenor et al. |
| 6,565,593 B2 | 5/2003 | Diana |
| 6,582,456 B1 | 6/2003 | Hand et al. |
| 6,705,388 B1 | 3/2004 | Sorgo |
| 6,713,733 B2 | 3/2004 | Kochman et al. |
| 6,723,115 B1 | 4/2004 | Daly |
| 6,730,115 B1 | 5/2004 | Heaton |
| 6,755,852 B2 | 6/2004 | Lachenbruch et al. |
| 6,770,848 B2 | 8/2004 | Haas et al. |
| 6,770,854 B1 | 8/2004 | Keane |
| 6,839,922 B1 | 1/2005 | Foggett et al. |
| 6,872,758 B2 | 3/2005 | Simpson et al. |
| 6,924,467 B2 | 8/2005 | Ellis et al. |
| 6,933,469 B2 | 8/2005 | Ellis et al. |
| 6,961,969 B2 * | 11/2005 | Nichols ............................ 5/420 |
| 6,967,309 B2 | 11/2005 | Wyatt et al. |
| 6,974,935 B2 | 12/2005 | O'Grady |
| 7,013,509 B2 | 3/2006 | Hickman |
| 7,020,912 B2 | 4/2006 | Berge |
| 7,022,950 B2 | 4/2006 | Haas et al. |
| 7,049,559 B2 | 5/2006 | Ishii et al. |
| 7,053,344 B1 | 5/2006 | Surjan et al. |
| 7,107,629 B2 | 9/2006 | Miros et al. |
| 7,161,120 B1 | 1/2007 | Stroud et al. |
| 7,176,419 B2 | 2/2007 | Ellis et al. |
| 7,181,790 B2 | 2/2007 | Wirtz |
| 7,228,578 B2 | 6/2007 | Linnane |
| 7,268,320 B2 | 9/2007 | Rock et al. |
| 7,282,676 B1 | 10/2007 | Bouchier et al. |
| 7,375,308 B2 | 5/2008 | Ferguson |
| 7,543,344 B2 | 6/2009 | Augustine et al. |
| 7,714,255 B2 | 5/2010 | Augustine et al. |
| 7,851,729 B2 | 12/2010 | Augustine et al. |
| 8,062,343 B2 | 11/2011 | Augustine et al. |
| 8,065,763 B2 | 11/2011 | Brykalski et al. |
| 8,170,685 B2 | 5/2012 | Docherty et al. |
| 8,283,602 B2 | 10/2012 | Augustine et al. |
| 8,288,693 B2 | 10/2012 | Weiss et al. |
| 8,291,612 B2 | 10/2012 | Ferguson |
| 8,418,297 B2 | 4/2013 | Mikkelsen et al. |
| 8,624,164 B2 | 1/2014 | Deibel et al. |
| 8,698,044 B2 | 4/2014 | Burr et al. |
| 8,772,676 B2 | 7/2014 | Augustine et al. |
| 8,876,812 B2 | 11/2014 | Aramayo |
| 2001/0020303 A1 | 9/2001 | Endo et al. |
| 2001/0044971 A1 * | 11/2001 | Borders ................. A61G 13/10 5/691 |
| 2002/0005398 A1 | 1/2002 | Gillner et al. |
| 2002/0047007 A1 | 4/2002 | Loyd, Sr. et al. |
| 2002/0073489 A1 | 6/2002 | Totton et al. |
| 2002/0117495 A1 | 8/2002 | Kochman et al. |
| 2002/0124312 A1 | 9/2002 | Yoon |
| 2003/0023292 A1 | 1/2003 | Gammons et al. |
| 2003/0069621 A1 | 4/2003 | Kushnir |
| 2003/0192121 A1 | 10/2003 | Fleming et al. |
| 2003/0195596 A1 | 10/2003 | Augustine et al. |
| 2003/0208848 A1 | 11/2003 | Flick et al. |
| 2004/0149711 A1 | 8/2004 | Wyatt et al. |
| 2004/0164499 A1 | 8/2004 | Murakami et al. |
| 2004/0174056 A1 | 9/2004 | Gryp et al. |
| 2004/0193237 A1 | 9/2004 | Krueger |
| 2004/0237206 A1 | 12/2004 | Webster et al. |
| 2005/0016982 A1 | 1/2005 | Campf et al. |
| 2005/0016993 A1 | 1/2005 | Koskey, Jr. |
| 2005/0051537 A1 | 3/2005 | Lewis |
| 2005/0061122 A1 | 3/2005 | Behringer |
| 2005/0061681 A1 | 3/2005 | Lim et al. |
| 2005/0103353 A1 | 5/2005 | Grahn et al. |
| 2005/0150763 A1 | 7/2005 | Butters et al. |
| 2006/0085919 A1 | 4/2006 | Kramer et al. |
| 2006/0120054 A1 | 6/2006 | Buschke |
| 2006/0142828 A1 | 6/2006 | Schorr et al. |
| 2006/0191675 A1 | 8/2006 | Fletcher et al. |
| 2006/0247745 A1 | 11/2006 | Thompson |
| 2006/0260060 A1 | 11/2006 | Apperson et al. |
| 2006/0261055 A1 | 11/2006 | Child et al. |
| 2007/0012675 A1 | 1/2007 | Devroy |
| 2007/0049997 A1 | 3/2007 | Fields et al. |
| 2007/0068916 A1 | 3/2007 | Augustine et al. |
| 2007/0068928 A1 | 3/2007 | Augustine et al. |
| 2007/0068929 A1 | 3/2007 | Augustine et al. |
| 2007/0068930 A1 | 3/2007 | Augustine et al. |
| 2007/0068931 A1 | 3/2007 | Augustine et al. |
| 2007/0068932 A1 | 3/2007 | Hewes et al. |
| 2007/0080155 A1 | 4/2007 | Augustine et al. |
| 2007/0093883 A1 | 4/2007 | Anderson et al. |
| 2007/0101996 A1 | 5/2007 | Carstens |
| 2007/0106353 A1 | 5/2007 | Carstens |
| 2007/0106355 A1 | 5/2007 | Carstens |
| 2007/0108190 A1 | 5/2007 | Ferguson |
| 2007/0152479 A1 | 7/2007 | Howman et al. |
| 2007/0164010 A1 | 7/2007 | Rock et al. |
| 2007/0243452 A1 | 10/2007 | Weidman et al. |
| 2007/0272673 A1 | 11/2007 | Keane |
| 2007/0284356 A1 | 12/2007 | Findlay |
| 2008/0021530 A1 | 1/2008 | Castellani et al. |
| 2008/0127414 A1 | 6/2008 | Allen |
| 2008/0173629 A1 | 7/2008 | Deibel et al. |
| 2008/0203080 A1 | 8/2008 | Fung |
| 2008/0217587 A1 | 9/2008 | Gaudiana et al. |
| 2008/0249521 A1 | 10/2008 | Dunning et al. |
| 2008/0249524 A1 | 10/2008 | Dunning |
| 2008/0255641 A1 | 10/2008 | Ellis |
| 2008/0281310 A1 | 11/2008 | Dunning et al. |
| 2008/0281311 A1 | 11/2008 | Dunning et al. |
| 2008/0283513 A1 | 11/2008 | Ferguson, III et al. |
| 2009/0036884 A1 | 2/2009 | Gregg et al. |
| 2009/0078690 A1 | 3/2009 | Lee et al. |
| 2009/0095735 A1 | 4/2009 | Resheff |
| 2009/0099631 A1 | 4/2009 | Augustine et al. |
| 2009/0163984 A1 | 6/2009 | Robinson et al. |
| 2009/0198230 A1 | 8/2009 | Behnke et al. |
| 2009/0222996 A1 | 9/2009 | Balonick et al. |
| 2010/0078807 A1 | 4/2010 | Schulz |
| 2010/0089896 A1 | 4/2010 | Bart |
| 2010/0119704 A1 | 5/2010 | Hemmelgarn et al. |
| 2010/0161016 A1 | 6/2010 | Augustine et al. |
| 2010/0168825 A1 | 7/2010 | Barbknecht |
| 2010/0200558 A1 | 8/2010 | Liu et al. |
| 2010/0204763 A1 | 8/2010 | Augustine et al. |
| 2010/0222457 A1 | 9/2010 | Wallner |
| 2010/0224612 A1 | 9/2010 | Asami et al. |
| 2010/0279086 A1 | 11/2010 | Park et al. |
| 2010/0283295 A1 | 11/2010 | Smith et al. |
| 2010/0325796 A1 | 12/2010 | Lachenbruch et al. |
| 2011/0031230 A1 | 2/2011 | Kim |
| 2011/0092930 A1 | 4/2011 | Poorman |
| 2011/0099900 A1 | 5/2011 | Weder |
| 2011/0233185 A1 | 9/2011 | Augustine et al. |
| 2012/0065716 A1 | 3/2012 | Gill et al. |
| 2012/0111846 A1 | 5/2012 | Hammerschmidt |
| 2012/0140375 A1 | 6/2012 | Kim et al. |
| 2012/0222192 A1 | 9/2012 | Carey et al. |
| 2012/0238842 A1 | 9/2012 | Colvin, Jr. et al. |
| 2012/0238901 A1 | 9/2012 | Augustine |
| 2012/0273475 A1 | 11/2012 | An |
| 2012/0279953 A1 * | 11/2012 | Augustine ............... A61G 13/12 219/217 |
| 2014/0074086 A1 | 3/2014 | MacIntyre-Ellis et al. |
| 2014/0263265 A1 | 9/2014 | Augustine et al. |
| 2014/0312027 A1 | 10/2014 | Augustine et al. |
| 2014/0316494 A1 | 10/2014 | Augustine et al. |
| 2014/0316495 A1 | 10/2014 | Augustine et al. |

(56) References Cited

U.S. PATENT DOCUMENTS

| | | |
|---|---|---|
| 2015/0148874 A1 | 5/2015 | Augustine et al. |
| 2015/0216610 A1 | 8/2015 | Augustine |
| 2015/0289817 A1 | 10/2015 | Augustine et al. |
| 2015/0290027 A1 | 10/2015 | Augustine et al. |
| 2015/0290062 A1 | 10/2015 | Augustine et al. |
| 2015/0327332 A1 | 11/2015 | Augustine et al. |
| 2015/0366367 A1 | 12/2015 | Augustine et al. |
| 2016/0143091 A1 | 5/2016 | Augustine et al. |

FOREIGN PATENT DOCUMENTS

| | | |
|---|---|---|
| EP | 787476 A2 | 8/1997 |
| EP | 1374822 A1 | 1/2004 |
| EP | 2662063 A1 | 11/2013 |
| GB | 586745 A | 3/1947 |
| GB | 969253 A | 9/1964 |
| WO | 9923992 A1 | 5/1999 |
| WO | 9925155 A | 5/1999 |
| WO | 0135878 A2 | 5/2001 |
| WO | 0195841 A2 | 12/2001 |
| WO | 2004093758 A1 | 11/2004 |
| WO | 2007041389 A1 | 4/2007 |
| WO | 2008089412 A1 | 7/2008 |
| WO | 2010107724 A1 | 9/2010 |
| WO | 2012125916 A2 | 9/2012 |
| WO | 2013134477 A1 | 9/2013 |
| WO | 2015157674 A2 | 10/2015 |
| WO | 2015157684 A1 | 10/2015 |

OTHER PUBLICATIONS

Bair Hugger brochure, retrieved from http://www.bairhugger.com/arizanthealthcare/pdf/600755A.pdf, 2003, 6 pages.

Lenhardt et al., "Local warming and insertion of peripheral venous cannulas: single blinded prospective randomised controlled trial and single blinded randomised crossover trial," British Medical Journal 325:409, Aug. 2002, 4 pages.

Invitation to Pay Additional Fees and, Where Applicable, Protest Fee for International Pat. App. No. PCT/US2015/025374, dated Jul. 20, 2015, 5 pages, European Patent Office, Rijswijk, The Netherlands.

International Search Report and the Written Opinion of the International Searching Authority, or the Declaration for International Pat. App. No. PCT/US2015/025374, dated Nov. 9, 2015, 5 pages, European Patent Office, Rijswijk, The Netherlands.

International Search Report and the Written Opinion of the International Searching Authority, or the Declaration for International Pat. App. No. PCT/US2015/025392, dated Jul. 16, 2015, 13 pages, European Patent Office, Rijswijk, The Netherlands.

International Patent Application No. PCT/US2015/060659, International Search Report and Written Opinion dated Feb. 5, 2016, 12 pages.

Moritz and Henriques, "Studies of Thermal Injury: The Relative Importance of Time and Surface Temperature in the Causation of Cutaneous Burns," Am. J. Pathology, vol. 23, 1947, pp. 695-720.

Stoll & Greene, "Relationship Between Pain and Tissue Damage Due to Thermal Radiation," J. Applied Physiology, vol. 14, No. 3, 1959, pp. 373-383.

Supplementary European Search Report for EP Pat. App. No. 12757173, dated May 22, 2015, 9 pages, European Patent Office, Munich, Germany.

* cited by examiner

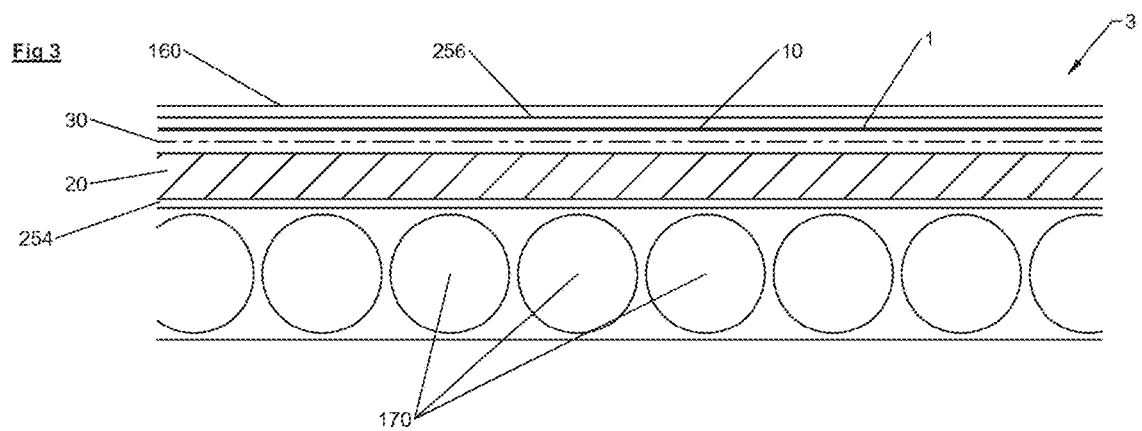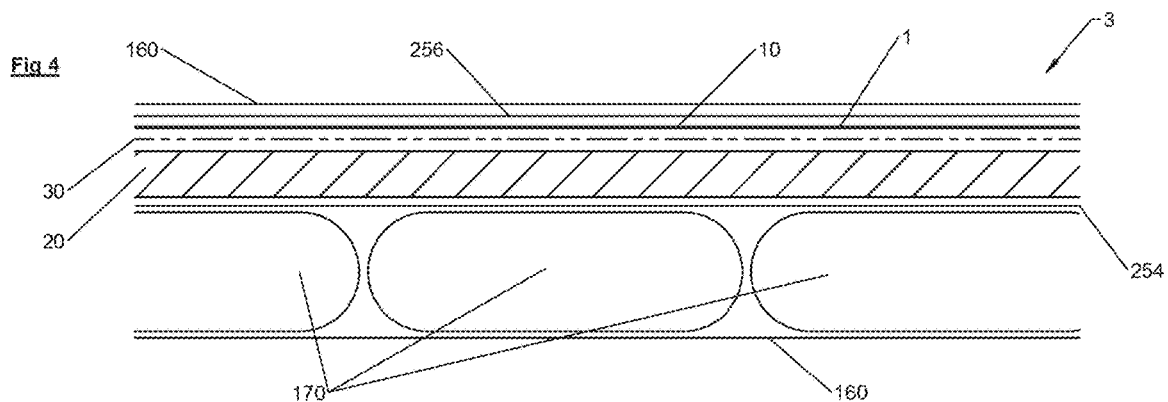

PATIENT SECURING OVERLAY FOR HEATED UNDERBODY SUPPORTS

RELATED APPLICATIONS

This application is a continuation application of U.S. patent application Ser. No. 15/918,311, filed Mar. 12, 2018 which is a continuation application of U.S. patent application Ser. No. 14/683,825, filed Apr. 10, 2015 which issued as U.S. Pat. No. 9,962,122 on May 8, 2018, which claims the benefit of U.S. Provisional Patent Application 61/977,930, filed Apr. 10, 2014, the entire contents of which are incorporated herein by reference.

This application is also a continuation of U.S. patent application Ser. No. 14/683,915, filed Apr. 10, 2015, which claims the benefit of U.S. Provisional Patent Application 61/977,930, filed Apr. 10, 2014, the entire contents of which are incorporated herein by reference.

BACKGROUND

Some underbody support mattresses for use during medical procedures use inflatable chambers as the support mechanism. The patient must be allowed to "sink" into the inflatable chambers if they are going to provide maximal surface contact with the patient's body in order to minimize the contact pressure at any given point, thus preventing pressure injury to the patient's skin. "Maximally" sinking into the inflatable chamber could be achieved by releasing air from the chamber until the moment before the most protruding body part of the patient touches the base layer of the mattress or the hard surface below the mattress. At this moment, the patient is maximally engulfed and supported by the mattress, much like floating in water. The problem is that there is currently no reliable way of determining when the most protruding patient part is near bottoming out versus actually touching the bottom.

Currently available underbody support mattresses with inflatable chambers adjust to a desired air pressure that is determined by the operator. Whether or not the patient sinks into the mattress and whether or not the body part that is most protruding "bottoms out" by touching the base layer of the mattress is totally a function of the operator guessing at the correct pressure setting. Some mattresses with inflatable chambers claim to analyze derivatives of the change in pressure to determine the optimal support pressure. However, none of these pressure-based control systems reliably allow the patient to sink maximally into the mattress until the most protruding body part is an optimal 0.5-1.0 inches from bottoming out. In this condition, all body parts are supported by air and yet the mattress maximally accommodates the patient's body for maximal contact pressure relief—similar to floating in water. There is a need for a better and more reliable control mechanism for reliably determining the maximum safe accommodation before any body part "bottoms out." Additionally, there is a need for a safety sensor that can detect changes in body positioning and/or loss of air from the inflatable chambers resulting in inadvertent "bottoming out," that may convert a safe condition into a dangerous condition over time, for example due to an air leak.

In addition, there are challenges to accurately measuring core body temperature through the skin and peripheral thermal compartment. There is a need for accurately and non-invasively measuring core body temperature during medical procedures such as surgery.

Grounding electrodes have been used during surgery for many decades. The electrical pathway for the radio-frequency (RF) electro-surgical units can be completed by directly applying a grounding pad to the patient's skin for direct electrical conduction. Alternately, grounding can be accomplished by placing a larger electrode under the patient which is not in direct electrical contact but rather creates a condition of capacitive coupling for grounding the RF electrical current, as described; for example, in U.S. Pat. Nos. 6,053,910 and 6,214,000. However, these capacitive coupling electrodes have been generally utilized as mattress overlays which are inconvenient, require extra cleaning and are usually embedded into a heavy, cumbersome gel pad.

Keeping the patient from sliding off of the surgical table when the table is tilted into a steep, head-down (Trendelenburg) position, is a constant challenge for surgical personnel and a danger for the patient. This problem has gotten worse in recent years with the advent of laparoscopic surgery and particularly with the advent of robotic surgery. In both of these instances, the patients are regularly placed into steep Trendelenburg so that gravity can move the internal organs out of the way of the laparoscopes. A reliable and convenient way of stabilizing the patient on the surgical table is needed for the Trendelenburg and other unusual positions.

SUMMARY

The underbody support mattresses of this disclosure are intended for use in medical settings generally. These include the operating room, the emergency room, the intensive care unit, hospital rooms, nursing homes and other medical treatment locations. They may also be used in other settings. Embodiments described in this application are related to U.S. Pub. Numbers 2012/0279953, 2012/0238901, and provisional application Nos. 61/812,987 and 61/936,508, the disclosures of all of which are incorporated herein by reference.

Various embodiments include flexible and conformable heated underbody supports including mattresses, mattress overlays, and pads for providing therapeutic warming to a person, such as to a patient in an operating room setting. In various embodiments, the heated underbody support is maximally flexible and conformable allowing the heated surface to deform and accommodate the person without reducing the accommodation ability of any under-lying mattress, for example.

In some embodiments, the heated underbody support includes a heater assembly and a layer of compressible material. The heater assembly may include a heating element including a sheet of conductive fabric having a top surface, a bottom surface, a first edge and an opposing second edge, a length, and a width. The conductive fabric may include threads separately and individually coated with an electrically conductive or semi-conductive material, with the coated threads of the fabric being able to slide relative to each other such that the sheet is flexible and stretchable. The heater assembly may also include a first bus bar extending along the entire first edge of the heating element and adapted to receive a supply of electrical power, a second bus bar extending along the entire second edge of the heating element, and a temperature sensor. The layer of compressible material may be adapted to conform to a person's body under pressure from a person resting upon the support and to return to an original shape when pressure is removed. It may be located beneath the heater assembly and may have a top surface and an opposing bottom surface, a length, and a width, with the length and width of the layer being approximately the same as the length and width of the heater assembly.

In some embodiments, the bus bars may preferably be braided wire. In some embodiments, it may be preferably to coat the bus bars with a flexible rubber material such as silicone rubber, during construction of the heater. While braided wire is relatively tolerant of repeated flexion, if the flexion occurs enough times at the same spot, even braided wire bus bars can fracture and fail. Coating the bus bars with silicone rubber can significantly increase the durability of the bus bars to survive repeated flexion.

In some embodiments, the conductive or semi-conductive material is polypyrrole. In some embodiments the compressible material includes a foam material and in some embodiments it includes one or more air filled chambers. In some embodiments, the heated underbody support also includes a water resistant shell encasing the heater assembly, including an upper shell and a lower shell that are sealed together along their edges to form a bonded edge, with the heater assembly attached to the shell only along one or more edges of the heater assembly. In some embodiments, the heating element has a generally planar shape when not under pressure. The heating element is adapted to stretch into a 3 dimensional compound curve without wrinkling or folding while maintaining electrical conductivity in response to pressure, and may return to the same generally planar shape when pressure is removed.

In some embodiments, the heated underbody support includes a heater assembly including a flexible heating element comprising a sheet of conductive fabric having a top surface, a bottom surface, a first edge and an opposing second edge, a length, and a width, a first bus bar extending along the first edge of the heating element and adapted to receive a supply of electrical power, a second bus bar extending along the second edge of the heating element, and a temperature sensor. The underbody support may further include a layer of compressible support material located beneath the heater assembly, which conforms to a patient's body under pressure and returns to an original shape when pressure is removed.

In some such embodiments, the heating element includes a fabric coated with a conductive or semi-conductive material, which may be a carbon or metal containing polymer or ink, or may be a polymer such as polypyrrole. In some embodiments, the heated underbody support also includes a shell including two sheets of flexible shell material surrounding the heater assembly, the shell being a water resistant plastic film or fiber reinforced plastic film with the two sheets sealed together near the edges of the heater assembly. In some embodiments, the heated underbody support also includes a power supply and controller for regulating the supply of power to the first bus bar.

In some embodiments, the compressible material comprises one or more flexible air filled chambers. In some such embodiments, the compressible material is a foam material. The heater assembly may be attached to the top surface of the layer of compressible material. In some embodiments, the heated underbody support includes a water resistant shell encasing the heater assembly and having an upper shell and a lower shell that are sealed together along their edges to form a bonded edge. In some such embodiments, one or more edges of the heater assembly may be sealed into the bonded edge. In some embodiments, the heater assembly is attached to the upper layer of water resistant shell material. In some embodiments, the heater assembly is attached to the shell only along one or more edges of the heater assembly.

In some embodiments, the heated underbody support also includes an electrical inlet, wherein the inlet is bonded to the upper shell and the lower shell and passes between them at the bonded edge.

In some embodiments, the heating element has a first Watt density when in a generally planar shape and a second Watt density when stretched into a 3 dimensional shape such as a compound curve, with the first Watt density being greater than the second Watt density.

In some embodiments, the temperature sensor is adapted to monitor a temperature of the heating element and is located in contact with the heating element in a substantially central location upon which a patient would be placed during normal use of the support. In some embodiments, the heated underbody support also includes a power supply and a controller for regulating a supply of power to the first bus bar.

In some embodiments, the heated underbody support is a heated mattress and includes a heater assembly and a layer of compressible material which conforms to a patient's body under pressure and returns to an original shape when pressure is removed located beneath the heater assembly. The layer of compressible material may include one or more inflatable chambers positioned under the heater assembly. A flexible, water resistant cover may encase the heater assembly, the layer of compressible material and the inflatable chambers.

In some embodiments, the heated underbody support may also include one or more additional inflatable chambers positioned under the layer of compressible material, with each of the inflatable chambers being elongated, having a longitudinal axis and optionally being positioned side-by-side one another with their longitudinal axes extending substantially from the first end to the second end of the support. In some embodiments, the inflatable chambers can be inflated and deflated in two groups while the support is in use, with the inflatable chambers being in alternating groups such that each inflatable chamber is in a different group from each inflatable chamber which is beside it.

In some embodiments, the heated underbody support includes a plurality of additional inflatable chambers. In some embodiments, the inflatable chambers can each be inflated and deflated independently while the support is in use. In some embodiments, the inflatable chambers can all be inflated and deflated simultaneously as a group while the support is in use. In some embodiments, the inflatable chambers can be inflated and deflated in two or more groups while the support is in use. In some embodiments, each of the chambers belongs to one of two or more groups, and the support includes separate conduits to each group with each conduit providing independent fluid communication to one of the groups of inflatable chambers for independently introducing or removing air from that group of inflatable chambers.

In some embodiments, the heated underbody support also includes a pressure sensor for measuring an actual internal air pressure of the groups of inflatable chambers, and a controller including a comparator for comparing a desired internal air pressure for each group of inflatable chambers with the actual internal air pressure of each group of inflatable chambers. The controller may be operatively connected to each of the conduits and to an air pump and may further include or be operatively associated with a pressure adjusting assembly for adjusting the actual internal pressure. The controller may be adapted to cause inflation or deflation of each group of inflatable chambers to adjust the actual internal air pressure of each of the group of inflatable chambers toward the desired internal air pressure.

In some embodiments, each inflatable chamber within each group of inflatable chambers is in fluid connection with every other inflatable chamber of its own group so that air pressure changes in one inflatable chamber redistribute to all of the other inflatable chambers in the same group. In some embodiments, an interface pressure is maintained on a top surface of each group of chambers at a location which supports a patient's body during normal use, the interface pressure being below a capillary occlusion pressure threshold of 32 mm Hg.

In some embodiments, an inflation characteristic, such as the volume of air within the inflatable chambers is controlled. Controlling the volume of air is different than other air mattresses that control the pressure within the inflatable chambers. It is impossible to detect changes in pressure as the patient begins to "bottom out" and therefore pressure control cannot reliably produce a state of "maximal accommodation" into the mattress.

In some embodiments the underbody support includes flexible, optionally radiolucent compression sensitive switches (e.g., compression sensing switches) within one or more of the inflatable chambers. These switches may be sized to detect when the patient has sunk into a partially inflated mattress to a point of "maximal accommodation." The switches may have a large surface area and may extend substantially the entire length of the inflatable chamber. These compression sensitive switches are positioned to detect a body part that is protruding down into the support mattress the furthest and to prevent that body part from "bottoming out" or touching the hard surface below the underbody support. The height of the inflatable chamber(s) at this point may be determined by the volume of the air in the chamber, not the pressure of the air in the chamber.

In some embodiments, the controller including a controller algorithm of the inflatable underbody support initiates the release of air from the inflated chambers after the patient is positioned on the support. The release of air allows the patient to sink into the support for maximal surface contact and therefore minimal surface contact pressure. Maximal surface contact occurs just before the most protruding body part "bottoms out" on the hard surface below. To achieve this, the air may be released from the inflatable chambers and the patient may be allowed to sink into the support until the most protruding body part reaches a predetermined distance from the bottom. At that point the most protruding body part may contact and close one or more of the switches.

In some embodiments the switch may be a compression switch, including a flexible compression sensitive switch. The switch may be radiolucent so as not to interfere with x-rays or other imaging systems. The closed switch may allow a small electric current to flow to the controller which may respond by stopping the air release and initiating the next sequence in the controller algorithm. In some embodiments, the controller algorithm then energizes the air pumps to re-inflate the inflatable chambers until the most protruding body part no longer compresses the compression sensitive switch(es) and the electric current no longer flows through the switch. In this position, the most protruding body part is accurately positioned at a predetermined distance above the hard base surface. With the compression sensitive switch(es) in the open position, it can then function as a safety sensor, detecting shifts in patient positioning or loss of air from the inflatable chambers that may result in inadvertent "bottoming out." Should the compression sensitive switch(es) close at this point, the controller algorithm may automatically add more air to the inflatable chambers until the switch(es) opens and/or may activate an alarm.

In some embodiments, the assembly of volume-controlled inflatable chambers is encased in a foam box-like structure. The box-like structure operating in conjunction with the inflatable chambers, creates a structure that allows the side walls to hinge inward for strain relief of the materials of the upper surface, in order to prevent "hammocking."

In some embodiments, one or more temperature sensors are interposed between the heated underbody support and the back or dependent body surface of the patient. The heated underbody support warms the peripheral thermal compartment of the patient that is in contact with the heated support surface of the underbody support, creating a condition of near thermal equilibrium between the core thermal compartment and the peripheral thermal compartment of the patient's back. In this situation, the skin temperature of the patient's back in contact with the heater accurately correlates with core body temperature.

In some embodiments, the underbody support includes a grounding electrode for electro-surgical equipment, such as capacitive coupling grounding electrodes as known in the art. This electrode may consist of a sheet of flexible and preferably stretchable conductive fabric that extends substantially across the entire surface area of the support mattress. Some electrodes have been supplied as mattress overlays and are generally incorporated into one or more layers of gel pads which can result in an overlay that is heavy, cumbersome and interferes with optimal pressure off-loading. To avoid these problems, various embodiments incorporate the electrode into the stack construction of the underbody support, eliminating the need for a heavy and cumbersome gel pad.

In some embodiments, the underbody support or the related heated electric blankets incorporate certain materials that can protect the polypyrrole heater (e.g., heating element 10), and other oxidizable electrical components not just from liquids, but also from oxidizing agents such as hydrogen peroxide ($H_2O_2$) disinfecting solutions. In some embodiments, urethane film may be used as the shell material for the underbody support or related blankets; however, urethane film is relatively permeable to hydrogen peroxide vapors, allowing the highly oxidizing vapors to enter the support or blanket. Once inside, the peroxide vapors may attack any oxidizable material. These vapors can cause oxidation and failure of electrical components, especially polypyrrole. In some embodiments, sacrificial materials are added that can be preferentially oxidized. Sacrificial materials are preferably organic materials such as cellulose. In some embodiments, materials that are known to be catalysts for the breakdown reaction of peroxide to water and oxygen may be added. For example, manganese dioxide ($MnO_2$) powder or other sacrificial material may be added to one or more of the fabric or foam layers or adhered to the heater with adhesive.

In some embodiments, the underbody support uses the fact that the patient sinks into the support and achieves maximal body surface contact with the support, to aid in preventing the patient from sliding off of the surgical table when placed in the steep Trendelenburg position (head down). In some embodiments, a sheet of fabric or other material that has been at least partially coated on both sides with high-friction plastic or rubber may be interposed between the patient and the support in order to increase the coefficient of friction. An example of this may be a PVC foam or silicone rubber applied as a pattern of three dimensional raised dots onto a fabric. In some embodiments, a foam cushion may be anchored to the head end portion 410 of the support and extend onto the mattress portion at the head end portion 410 of the surgical table 412 for added safety.

In some embodiments, the underbody support includes a layer of water-circulating channels over the surface area of the underbody support. Cold water can be circulated through these channels for inducing therapeutic hypothermia or therapeutic cooling.

BRIEF DESCRIPTION OF THE DRAWINGS

FIGS. 3-4. are cross-sectional views of an underbody support with optional heater assembly in accordance with illustrative embodiments.

DETAILED DESCRIPTION

Figure 1:
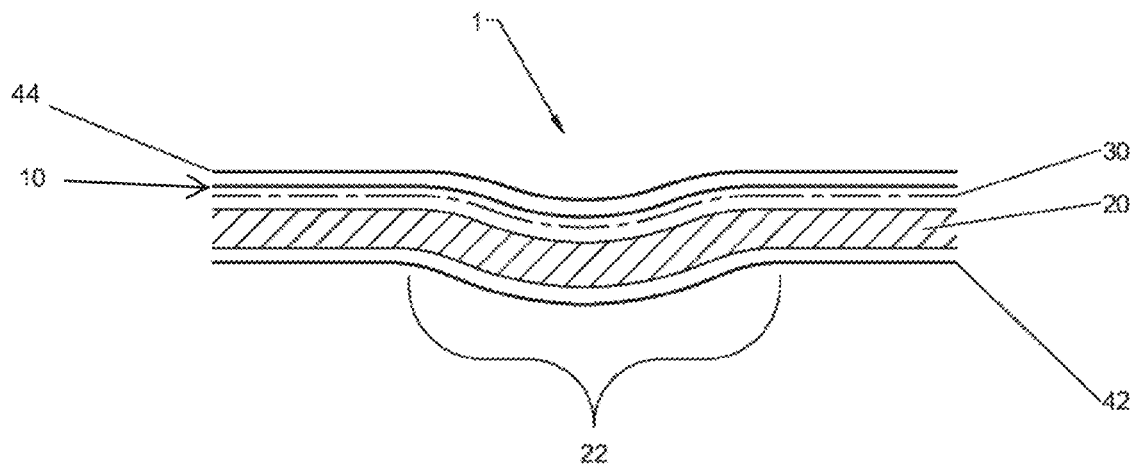
FIG. 1 is a cross-sectional view of a heater assembly in accordance with illustrative embodiments.

The following detailed description is exemplary in nature and is not intended to limit the scope, applicability, or configuration of the invention in any way. Rather, the following description provides practical illustrations for implementing various exemplary embodiments. Examples of constructions, materials, dimensions, and manufacturing processes are provided for selected elements, and all other elements employ that which is known to those of skill in the field. Those skilled in the art will recognize that many of the examples provided have suitable alternatives that can be utilized.

Embodiments include underbody supports such as heated underbody supports, including heated mattresses, heated mattress overlays, and heated pads. The term underbody support may be considered to encompass any surface situated below and in contact with a user in a generally recumbent position, such as a patient who may be undergoing surgery, including heated mattresses, heated mattress overlays and heated pads.

Heated mattress overlay embodiments may be identical to heated pad embodiments, with the only difference being whether or not they are used on top of a mattress. Furthermore, the difference between heated pad embodiments and heated mattress embodiments may be the amount of support and accommodation they provide, and some pads may be insufficiently supportive to be used alone like a mattress. As such, the various aspects which are described herein apply to mattresses, mattress overlay and pad embodiments, even if only one type of support is shown in the specific example.

While there is repeated reference to "heated underbody supports" in this disclosure, it must be noted that the heat feature is not a necessary component of every embodiment. Non-heated underbody support embodiments are also anticipated.

Various embodiments improve patient warming effectiveness by increasing accommodation of the patient into the heated mattress, mattress overlay, or pad, in other words, by increasing the contact area between the patient's skin and the heated surface of the mattress or mattress overlay. The heating element, and the foam or inflatable chambers (e.g., air bladders) of the mattress, which may also be included, are easily deformable to allow the patient to sink into the mattress, mattress overlay, or pad. This accommodation increases the area of the patient's skin surface in contact with the heated mattress, mattress overlay, or pad and minimizes the pressure applied to the patient at any given point. It also increases the surface contact area for heat transfer and maximizes blood flow to the skin in contact with the heat for optimal heat transfer. The accommodation of the patient into the mattress, mattress overlay, or pad is not hindered by a stiff, non-conforming, non-stretching, hammocking heater. Additionally, in various embodiments, the heating element is at or near the top surface of the underbody support, in thermally conductive contact with the patient's skin, not located beneath thick layers of foam or fibrous insulation.

Figure 2:
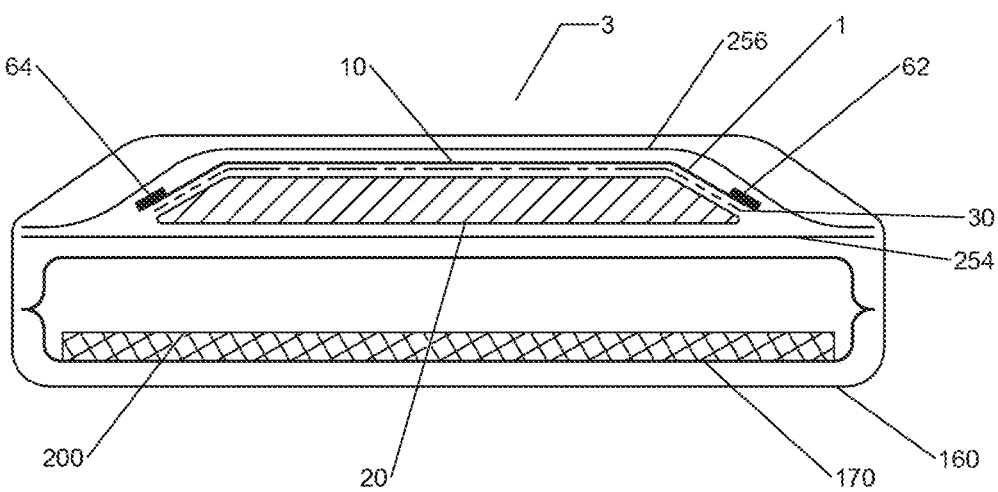
FIG. 2. is a cross-sectional view of an underbody support in accordance with illustrative embodiments, including the heater assembly of FIG. 1.

As shown in FIGS. 1-2, the combination of the thermal warming effectiveness and the skin pressure reduction effectiveness of a heated underbody support 3 (e.g., FIGS. 2, 19 and 23) can be optimized when a heating element 10 is overlaying a layer, such as a compressible material layer 20, that can provide maximal accommodation 22 of a patient (e.g., FIG. 23) positioned on the underbody support 3 (e.g., mattress).

In this condition, the heating element 10 is in contact with a maximal amount of the patient's skin surface 232 which maximizes heat transfer and pressure reduction. Heated underbody supports 3 made with inflatable chambers 170 (FIG. 2) forming or included in the compressible material layer 20, or in addition to the compressible material layer 20, can also provide excellent accommodation. Further, a heated underbody support 3 with excellent accommodation properties having a heating element 10 as described herein avoids degrading the accommodation properties of the underbody support 3 when a heater assembly 1 is added or included. Therefore, the combination of the heater assembly 1 design with an accommodating underbody support 3, made with one or more inflatable chambers 170, is advantageous and synergistic for the effectiveness of both technologies. However, all features described herein may be used independently, or in combination with one another. For example, the underbody support 3 described herein may or may not be: heated, include grounding, have hydrogen peroxide protection, patient securing features, water circulating channels, or any other features described herein. Likewise, the heater assembly 1 described herein may or may not include: an underbody support 3, include grounding, have hydrogen peroxide protection, patient securing features, water circulating channels, or any other feature described herein. Illustrative examples are provided, and all possible combinations of the features herein are considered embodiments of this disclosure.

As shown in FIG. 1, some embodiments of the heater assembly 1 include a heating element 10 coupled by a layer of adhesive 30 to the layer of compressible material 20. The heating element 10, the layer of compressible material 20 and the adhesive 30 may then be encapsulated and sealed by upper and lower shells 42, 44. The seal may be a hermetic seal.

In some embodiments, as shown in FIG. 2, bus bars 62, 64 of the heating element 10 are optionally made of braided wire. While braided wire is relatively tolerant of repeated flexion, if the flexion occurs enough times at the same spot, even braided wire bus bars can fracture and fail. In some embodiments, the bus bars 62, 64 may be braided wire bus bars 62, 64 and may be coated with a flexible rubber-like material such as silicone. The coating may be applied during construction of the heater assembly 1.

Coating the bus bars 62, 64 with silicone can vastly increase the durability of the bus bars 62, 64 to repeated flexion. The silicone or other coating can serve at least two functions, first, it forces the individual wire strands to form a larger radius during flexion and second, it stabilizes the individual wire strands so that they do not abrade each other during flexion. Thicker coats of silicone rubber or other material on the bus bars 62, 64 may provide more protection from flexion fractures than thin coats.

Our testing has shown that braided bus bars, like bus bars 62, 64, sewn in parallel on a heating element 10 made from a piece heater material such as a non-woven heater fabric, can be repeatedly and bent or flexed at a specific point. During testing all of the bus bars were flexed along a single crease in the heater fabric, through a 360° arc, gently creasing the bend and then flexing it in the other direction though a 360° arc. This process was repeated until the bus bars failed at the bend. Uncoated and thinly coated bus bars began to fail at approximately 350 flexions and totally failed by 450 flexions. Bus bars with a "medium" coating of silicone rubber (approximately 1/32 inches thick) failed between 1900 and 2100 flexions. Bus bars with a "thick" coating of silicone rubber (approximately 1/16 inches thick) showed no signs of failure after 2500 flexions.

FIGS. 2, 3 and 4 show an embodiment of an underbody support 3 comprising one or more inflatable chambers 170 (e.g., air chamber, fluid chamber), and a heater assembly 1 overlaying the one or more inflatable chambers 170. In some embodiments, a single inflatable chamber 170, or a plurality of elongated inflatable chambers 170 are positioned under the heater assembly 1. The plurality of elongated inflatable chambers 170 may be cylindrical in shape and may be oriented in parallel and positioned side-by-side one another, with their long axes extending substantially from one side of the underbody support 3 mattress to the other side. However, other inflatable chamber 170 shapes and orientations are anticipated. The inflatable chambers 170 may be round or ovoid in cross section. They may or may not be physically secured to an adjacent inflatable chamber 170. Alternately, they could be secured to a base sheet or simply positioned and contained within a cover 160 (e.g., mattress cover) without being secured. The inflatable chambers 170 may be made of a fiber-reinforced plastic film or a plastic film that has been bonded, laminated or extruded onto a woven or non-woven fabric reinforcing layer. Urethane may be used as the plastic film, but other plastic film materials are anticipated. Woven nylon may be used as the reinforcing layer, but other fabric materials are anticipated. The inflatable chambers 170 may also be used for pressure reduction alone, in an underbody support 3 without a heater assembly 1 or heating element 10.

The inflatable chambers 170 can be sealed and static, or connected together in fluid connection to allow redistribution of air between the inflatable chambers 170. In some embodiments, the inflatable chamber 170 can be actively inflated and deflated while the underbody support 3 is in use. The inflatable chambers 170 may be inflated and deflated each independently, all simultaneously, or in separate groups, while the underbody support 3 is in use. In some embodiments, the inflatable chambers 170 are each a part of two separate groups and may be segregated, for example, by every other inflatable chamber 170 (e.g., alternating inflatable chambers 170) according to their relative side-by-side positions. A conduit or conduits may be in separate independent fluid communication with each inflatable chamber 170 of the group of inflatable chambers 170 for independently introducing or removing air from that group of inflatable chambers 170.

Alternately, there may be only a single group of inflatable chambers 170 or there may be more than two groups of inflatable chambers 170 which can be separately inflated or deflated. If multiple groups of inflatable chambers 170 are used, they may or may not be evenly or symmetrically arranged. For example, inflatable chamber 170 groups may be separated according to the amount of weight-bearing associated with that area. Inflatable chambers 170 in greater weight bearing areas, such as the torso and hips, may be in a first group, while inflatable chambers 170 in areas bearing less weight, such as those supporting the head and legs, may be a separate group of inflatable chambers 170. In this way, the lighter portions of the patient's body may be supported by inflatable chambers 170 that are inflated to a lower air pressure than inflatable chambers 170 that support more weight/heavier body portions.

Inflatable chambers 170 may be secured to the adjacent inflatable chamber 170 or to a base sheet or may be secured by the ends to an element running along each side of the underbody support 3, and in some embodiments the inflatable chambers 170 and their connectors for fluid connection may be individually detachable. In this instance, if a single inflatable chamber 170 or connector fails or is damaged, it can be replaced without requiring the replacement of the entire inflatable underbody support 3.

The material forming the inflatable chamber 170, such as a plastic film, may be bondable with RF, ultrasound, heat, solvent, or other bonding techniques. The film or film layer of the laminate may be folded back on itself and a single longitudinal and two end bonds that may cooperate to form an inflatable chamber 170. More complex inflatable chamber 170 construction and bonding embodiments are anticipated.

The conduit fluid connection for air flow to and from and between the inflatable chambers 170 may be plastic tubing, for example. The inlet into the inflatable chamber 170 can be through one of the bonded seams or may be through a surface of the inflatable chamber 170. To prevent occlusion of the tubing at the inlet, the tubing may extend one or more inches into the inflatable chamber 170. Other conduits are anticipated, such as a molded or inflatable plenum that may run the length of the underbody support 3.

Figure 5:
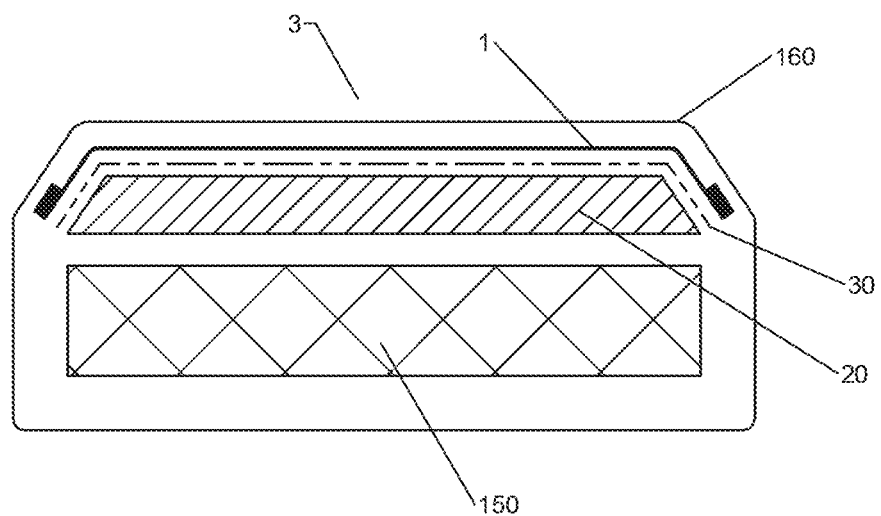
FIG. 5 is a cross-sectional view of an underbody support with optional heater assembly in accordance with illustrative embodiments.

In some embodiments such as FIG. 2, a heater assembly 1 (a heater assembly 1 encased within a water resistant shell 42, 44) is placed on top of the inflatable chambers 170 so that the conductive fabric heating element 10 is at or near the top surface of the underbody support 3. Alternately such as shown in FIG. 5, a heater assembly 1 (without a shell 42, 44) could be placed on top of the inflatable chambers 170 so that the heating element 10 is at or near the top surface of the underbody support 3 mattress. The underbody support 3 may include a flexible, water resistant cover 160 that encases the heater assembly 1 and the inflatable chambers 170. Alternately as shown in FIG. 5, heater assembly 1 could be placed on top of a polymeric foam pad 150 such as viscoelastic or urethane foam. In some embodiments the inflatable chambers 170 may be used as an underbody support 3 mattress without a heater assembly 1.

In some embodiments, the water resistant cover 160 is a plastic film laminated or extruded onto a woven or knit fabric such as "Naugahyde." This construction is soft and durable. Alternately, the cover 160 can be made of plastic film, fiber-reinforced plastic film or a plastic film laminated or bonded to a woven, non-woven, or knit fabric. Covering 160 made of plastic film laminated or extruded onto a woven or knit fabric may include sealed seams such as RF, ultrasound or heat, if the plastic film side is inverted into the seams so that layers of plastic film are in opposition to each other. Alternately, the polymer coated fabric is well-suited to a sewing process for creating the seams. Seams created by a sewing process may advantageously include an adhesive bond for sealing the sewn seam against liquid intrusion.

The heater assembly 1 of the underbody support 3 may be "free floating" within the water resistant cover 160 of the underbody support 3. Alternately, the heater assembly 1 may be attached to the inflatable chamber 170 or foam pad 150, or attached to the cover 160, either at the edges of the heater assembly 1 or on or across the top or bottom surface of the heater assembly 1.

One or more edges of the heater assembly 1, such as two or four edges, may be attached to the ends of the elongated inflatable chambers 170 or compressible material layer 20 by snaps, Velcro or any other suitable forms of attachment. Such embodiments may stabilize the heater assembly 1 within the underbody support 3. A series of independent securing tabs or flaps may extend laterally from the bonds 48 of the heater assembly 1 encapsulation shell 42, 44. As the inflatable chambers 170 inflate and become turgid, they simultaneously stretch the heater assembly 1 laterally, assuring that the heating element 10 cannot wrinkle and fold on itself or become displaced.

In some embodiments, an inflation characteristic such as the volume of air within the inflatable chambers 170 is controlled. Controlling the volume of air is different than all other air mattresses known to the instant inventors that control the pressure within the inflatable chambers 170. In other systems, it is impossible to detect changes in pressure as the patient begins to "bottom out" and therefore pressure control cannot reliably produce a state of "maximal accommodation" into the mattress. In contrast, controlling for and measuring an inflation characteristic (e.g., air volume, indication of near collapse, a distance between portions of the inflatable chamber 170) in the most depressed inflatable chamber 170 with an appropriate sensor, can insure "maximal accommodation." "Maximal accommodation" is the point when the patient has maximally sunk into the underbody support 3, but has not yet touched the hard base with their most protruding body part 230 (e.g., FIGS. 8-11). A variety of sensing technologies for determining air volume within the inflatable chambers 170 may be used in various embodiments.

Figure 6:
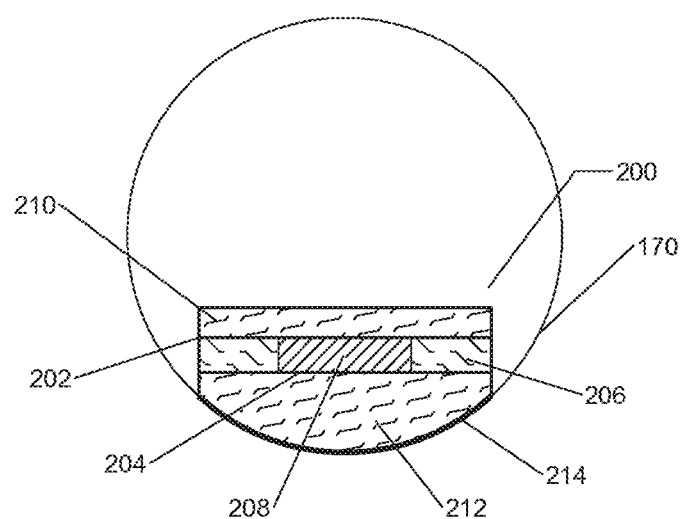
FIGS. 6-7 are cross-sectional views of an inflatable chamber including a sensing device in accordance with illustrative embodiments.
Figure 7:
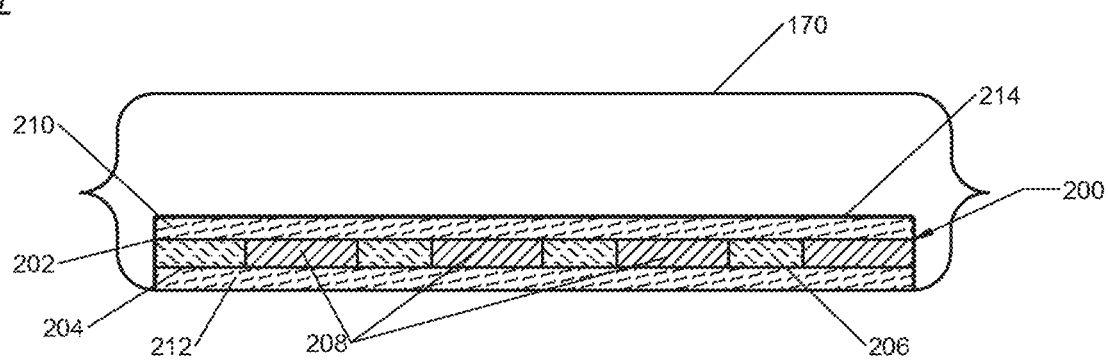

As in FIGS. 6 and 7, some embodiments of the underbody support 3 include sensing devices such as switches 200. Switches 200 may be flexible, radiolucent compression sensing devices within one or more of the inflatable chambers 170. In some embodiments, switches 200 may be other types of switches other than flexible, radiolucent compression sensitive switches. The switches 200 may be positioned to sense the patient body part that is protruding down into the underbody support 3 the furthest and to prevent that body part from "bottoming out" or touching the hard surface below the underbody support 3. Since the "most protruding body part," or portion of the body sinking deepest into the underbody support 3 (e.g., element 230, FIGS. 8-11), is unpredictable (buttocks, hip, elbow, shoulder), the location of the most protruding body part on the underbody support 3 is also unpredictable. Therefore, the switches 200 are preferably located in each of the inflatable chambers 170 and have a large surface area relative to the inflatable chamber 170 size.

In the embodiment of FIGS. 6 and 7, the compression sensitive switches 200 are sized and shaped to fit the size and shape of the inflatable chamber 170 and to activate at a given volume of air that correlates with the height thickness of the switch 200. In the case of a tubular inflatable chamber 170, the switches 200 are preferably relatively wide, covering 0.3-0.7 of the diameter of the inflated inflatable chamber 170 (FIG. 6) and preferably extending substantially the entire length of the inflatable chamber 170 (FIG. 7). For example, if the inflatable chamber 170 is 3 inches in diameter and is 18 inches long, the surface area of the switch 200 may be 1-2 inches wide and 16 inches long. Other switch 200 widths and lengths are anticipated. The relatively large surface area of the individual switches 200, and the arrangement of the individual switches 200 into a pattern may cover substantially the surface area of the underbody support 3. This assures that the "most protruding body part" at any location on the surface of the underbody support 3 can be detected.

The compression sensitive switches 200 may be physically located within the inflatable chamber(s) 170, so that they are protected from random compression by the adjacent inflatable chamber 170, when the inflatable chamber 170 is inflated and the underbody support 3 is in use. In some embodiments, being located within the inflatable chamber 170 also protects the switch 200 from damage. It also assures that the compression sensitive switch 200 is contacted by "the most protruding body part" 230 (FIGS. 8-11) at a precise height above bottoming out against the hard base, or above the bottom of the inflatable chamber 170 or other surface, which allows maximum accommodation of the patient 230 (FIGS. 8-11) into the underbody support 3 and yet protects against bottoming out. For example, in FIGS. 8 and 9, if the inflatable chamber 170 has a cross-sectional diameter of 3 inches, the switch 200 may preferably be designed to sense contact when "the most protruding part" of the patient 230 is 0.75-1.0 inches above bottoming out. This height correlates with a given volume of air in the inflatable chamber 170. Other switch contact heights are anticipated which correlate with other volumes of air. If additional accommodation of the patient into the support is desirable, the switch 200 may be designed to sense contact at a height of less than 0.75 inches. If added safety is desired, the switch 200 may be designed to sense contact at a height of more than 1.0 inches. While the compression sensitive switches 200 disclosed herein may be preferred, other types and construction of switches, including volume measuring switches and distance measuring switches are anticipated.

Other switches 200, such as pressure-sensing membrane switches are well-known in the art. Pressure-sensing membrane switches generally consist of two separated metal foil contacts that can be pressed together to make contact in response to applied pressure. The precise positioning of the metal foil is determined by the shape of the stiff plastic film (membrane) to which the foil is applied. These switches are minimally flexible because flexion may cause the metal foil contacts to close in the absence of applied pressure. These membrane switches are hard, generally made of a stiff plastic film adhered to a hard surface like metal or glass in order to protect the fragile metal foil contacts. Finally, the metal foil conductors and contacts are radio-opaque, meaning that they show up on x-ray. While these pressure sensing membrane switches may be used in various embodiments, the switches 200 used in various embodiments may alternatively be flexible, radiolucent, durable compression sensitive switches, and not require mounting to a hard surface to assure proper functioning. The instant invention may use any other suitable type of switch.

As shown in FIGS. 6-9, the compression sensitive switches 200 of the instant invention may use electrically conductive fabric pieces as the conductor and/or contacts 202, 204. The conductive fabric pieces (e.g., 202, 204) may be polypyrrole coated onto any woven or non-woven fabric. Alternately, the conductive fabric in the switch 200 may be carbon fiber fabric or fabric that has been coated with conductive ink or metal such as silver. Alternately, the conductor 202, 204 in the switch 200 may be conductive ink applied to polymeric film or conductive materials such as carbon or metal impregnated into polymeric films.

For the following description, it is assumed that the inflated inflatable chamber 170 is a tube that is approximately 3 inches in diameter and 18 inches long as in FIGS. 6 and 7. However, the size and shape of the compression sensitive switches 200 may change for inflatable chambers 170 of other sizes and shapes. The contacts 202, 204 and conductors of the switch 200 may include two pieces of conductive fabric. In this example, each of the two pieces of the conductive fabric contacts 202, 204 may be 1.5 inches wide and 16 inches long. The two conductive fabric contacts 202, 204 may be adhesively bonded to both sides of a strip of compressible material that forms a compressible switch layer 206. The compressible switch layer 206 may be a resilient open-cell foam material, such as urethane foam. However, other materials such as polymeric foam materials or high-loft fibrous materials may be used.

In some embodiments, the compressible switch layer 206 may be 3/16-3/4 inches thick, however, other thicknesses of compressible switch layers 206 may be used. One or more holes 208 may be cut through the compressible switch layer 206. Preferably, a pattern of multiple holes 208 may be cut through the compressible switch layer 206. The size and shape of the holes 208 may be determined by the thickness, size, shape and compressibility of the compressible switch layer 206. For example, if the compressible switch layer 206 is 3/16 inch thick, the holes 208 may be 1/2-3/4 inches in diameter. If the compressible switch layer 206 is 3/4 inches thick, the holes 208 may be 3/4-1 inch in diameter. Embodiments include holes 208 of various number, shape, size and pattern.

In the embodiment of FIGS. 6 and 7, the compression sensitive switches 200 may also include two layers of compressible foam. An upper compressible foam layer 210 and a lower compressible foam layer 212, sandwiching the conductive fabric pieces/contacts 202, 204 and the compressible switch layer 206 there-between. The compressible foam layers 210, 212 may be attached to the conductive fabric pieces/contacts 202, 204 with adhesive forming a five-layer sandwich construction. The compressible foam layers 210, 212 may be 1/4-1/2 inches thick but other thicknesses may be used. Many foam materials are suitable including open cell urethane. While foam may be used for these layers, other materials such a high-loft fibrous materials may also be used. The lower compressible foam layer 212 that is positioned on the bottom side of the switch 200 may be tapered toward its long edges in order to seat in the curved shape of the inflated inflatable chamber 170. Curving the lower compressible foam layer 212 allows the conductive fabric pieces 202, 204 and the compressible switch layer 206 (the active part of the switch) to remain relatively flat, despite being located within a curved chamber.

Figure 8:
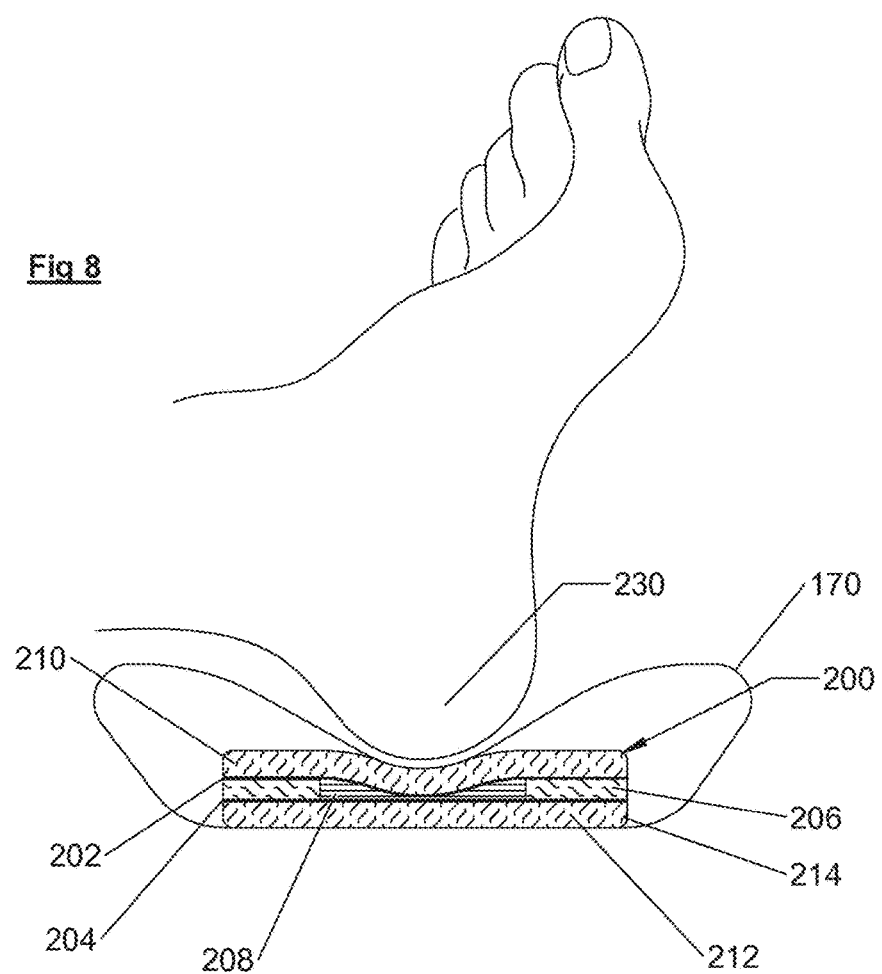
FIGS. 8-11 are cross-sectional views of an inflatable chamber in accordance with illustrative embodiments and a protruding part of the patient.
Figure 9:
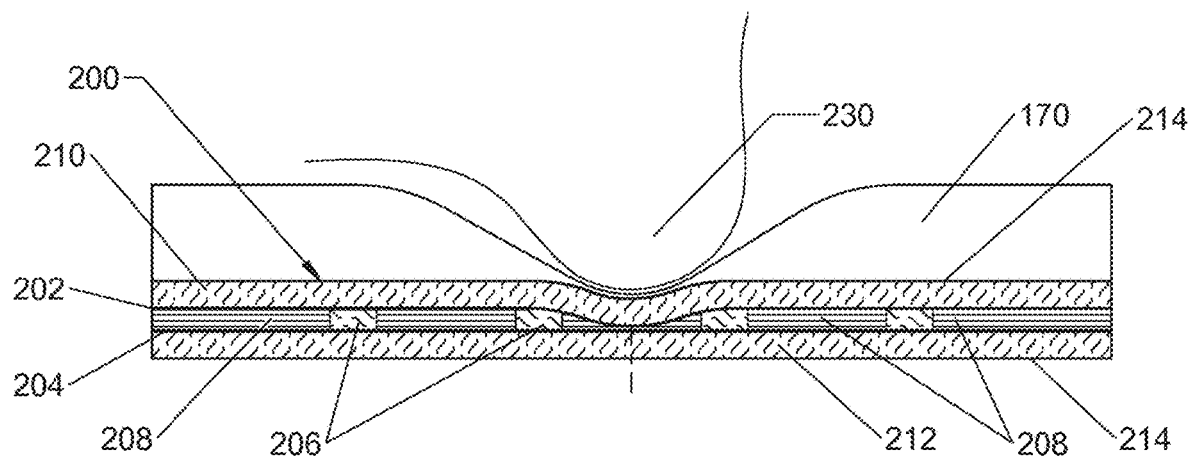

When the compressible switch layer 206 is compressed as shown in FIGS. 8 and 9, the two pieces of conductive fabric 202, 204 contact each other within the space(s) created by the one or more holes 208. A wire conductor may be attached to each of the conductive fabric contacts/pieces 202, 204. A small electric potential is applied to the conductive fabric contacts/pieces 202, 204 and when they contact each other, an electric current flows through the switch 200, activating the controller.

The controller may be activated by active feedback data derived from the current flowing through one or more of the compressed compression sensitive switches 200. This signal allows the system to maintain a desired internal air volume within the most depressed inflatable chamber 170 by adjusting the amount of inflation of the most depressed inflatable chamber 170 or of the groups of inflatable chambers 170, such as first and second groups of inflatable chambers 170. Controlling the air volume in the most depressed inflatable chamber 170 independent of air pressure, allows maximal accommodation of the patient 230 into the inflatable underbody support 3. This is in contrast to all other air-filled support mattresses and air-filled support surfaces known to the instant inventors, which rely on controlling air pressure.

Figure 12:
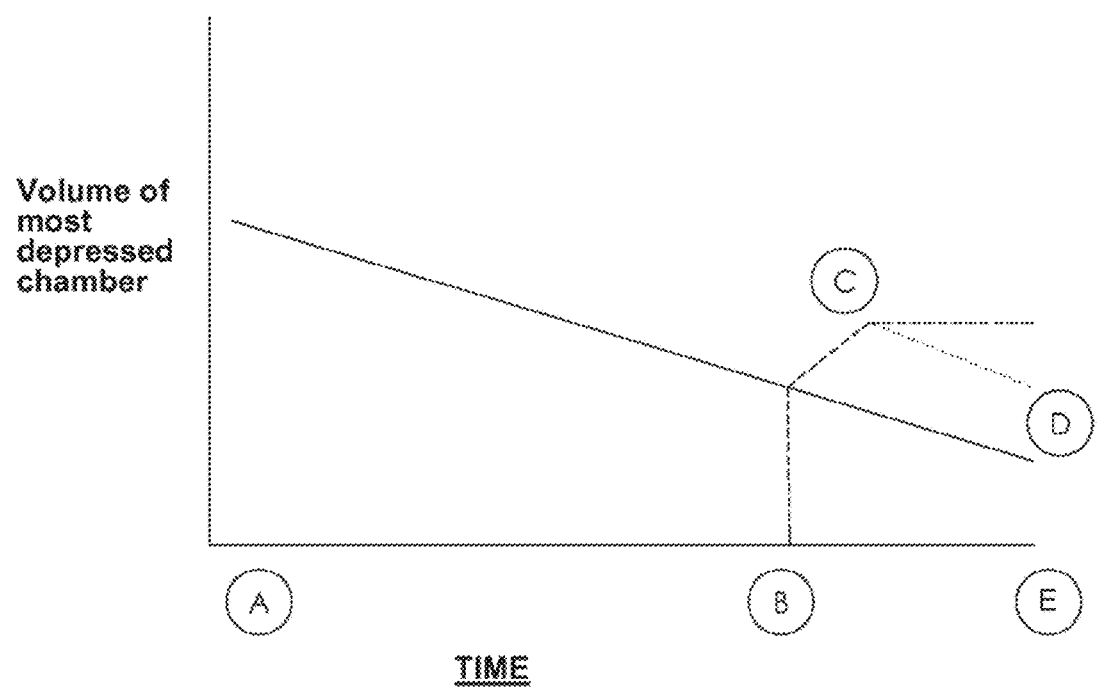
FIG. 12 is an illustrative plot of the volume of a most depressed inflatable chamber vs. time in accordance with illustrative embodiments.

FIG. 12 illustrates the volume vs. time curve measured when air is released from the most depressed inflatable chamber 170 with a patient laying on the underbody support 3 mattress. This allows the patient to progressively sink into the underbody support 3, which if carried to a conclusion would result in the patient laying on the hard base layer without any air there between at point E. However, when the volume decreases to the point B where the compression sensitive switch(es) 200 is compressed in the most depressed inflatable chamber 170, deflation is reliably stopped before the patient "bottoms out," point E. This condition is also illustrated in FIGS. 8 and 9.

Figure 13:
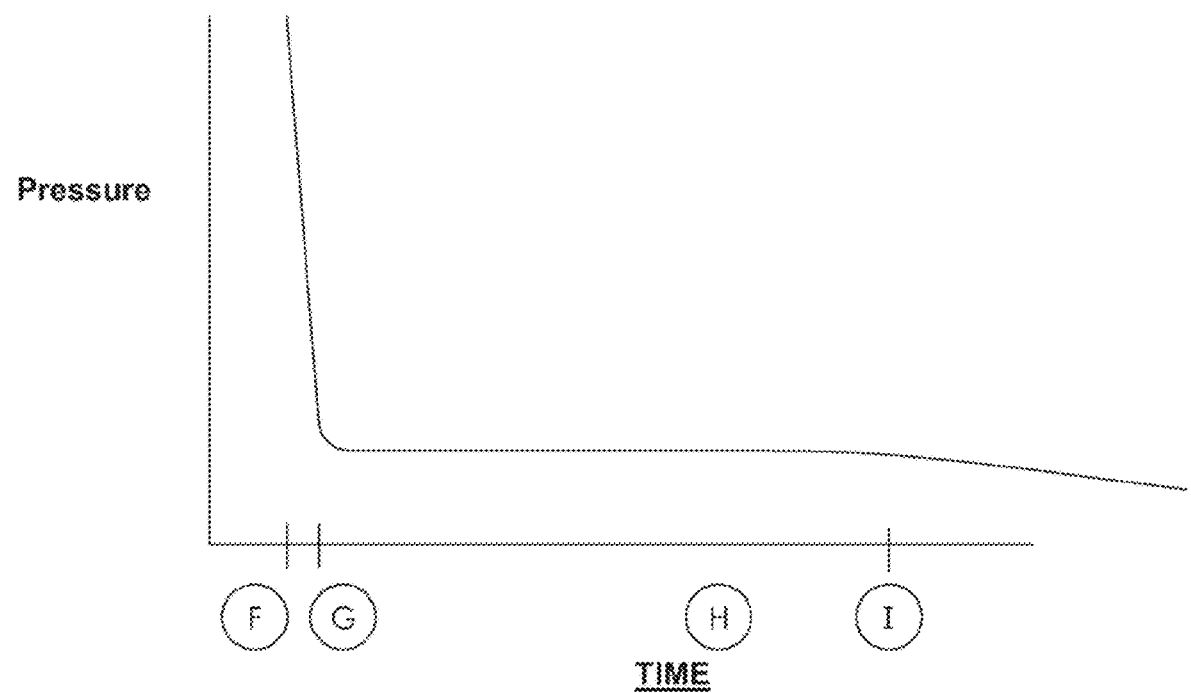
FIG. 13 is an illustrative plot of air pressure in an inflatable chamber vs. time in accordance with illustrative embodiments.
Figure 14:
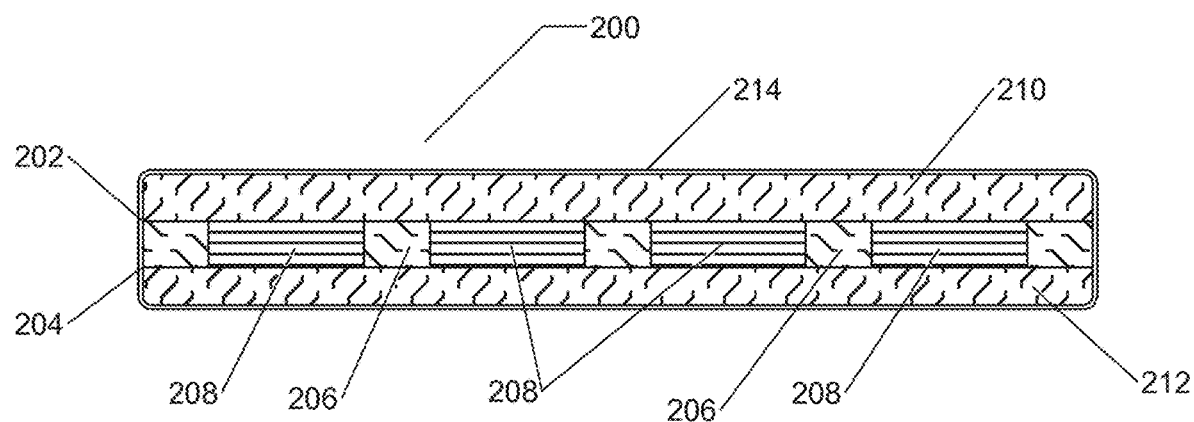
FIG. 14 is a cross-sectional view of a compressive sensing switch in accordance with illustrative embodiments.
Figure 15:
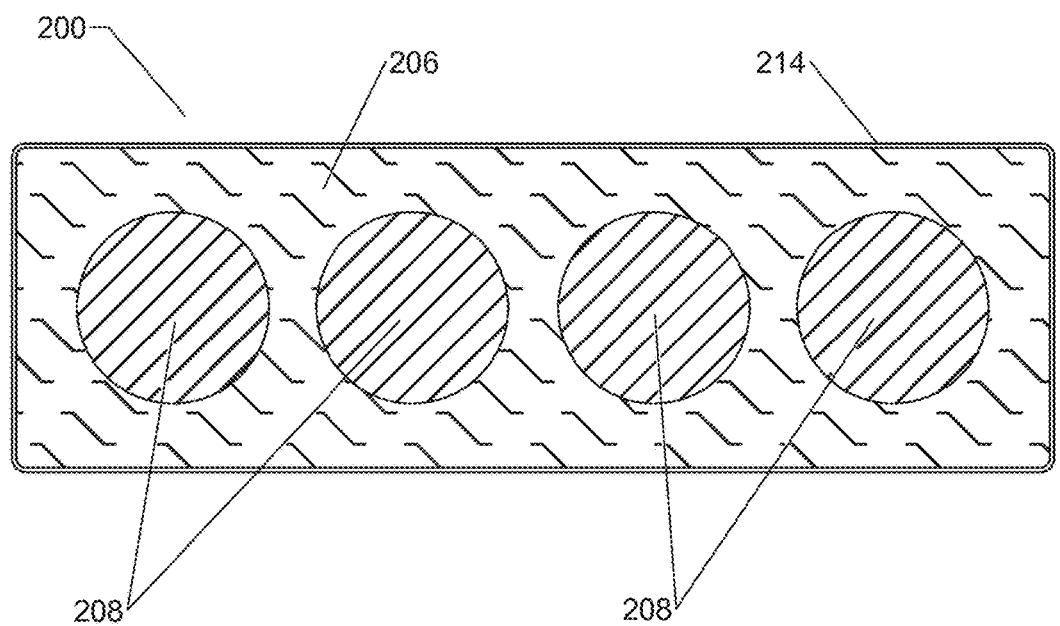
FIG. 15 is a top view of the compressive sensing switch of FIG. 14 in accordance with illustrative embodiments.

In contrast, FIG. 13 illustrates the pressure vs. time curve measured when air is released from the inflatable chambers 170 with a patient laying on the underbody support 3. This allows the patient to progressively sink into the underbody support 3, which if carried to a conclusion would result in the patient laying on the hard base layer without any air there between. At time F, the chambers 170 are inflated to a pressure that is higher than the pressure exerted by the weight of the patient. With deflation, the pressure gradually drops and at time G the pressure in the underbody support 3 is determined by the weight and geometry of the patient. With continued deflation, the pressure remains substantially unchanged as the patient continues to sink into the deflating underbody support (GI). At time H, the most protruding point of the patient 230 (FIGS. 8-11) bottoms out on the hard base layer; however, no change in pressure is noted despite "bottoming out" having occurred. A reduction in measured pressure is not noted until time I, when a majority of the patient is "bottomed out" and is resting on the hard base layer of the underbody support 3.

From FIG. 12, it is apparent that the precise switch 200 closure at time B as shown in FIGS. 8 and 9, indicating that the appropriate "maximal accommodation" volume has been reached, is a safe and reliable way to optimally support the patient. In contrast, the subtle changes in pressure shown in FIG. 13 cannot be reliably detected and do not correlate with the "bottoming out" (H) of the patient's most protruding part. Therefore, it should be evident that controlling the inflatable chambers 170 of this support surface by detecting and controlling air volume is a significant improvement in reliability and safety compared to the standard method of detecting and controlling air pressure.

Alternately, or additionally, the inflatable underbody support 3 may include pressure sensor assemblies capable of detecting, in real time, the actual internal air pressure of the inflatable chambers 170 and may also include a comparator which may be in operational communication with the controller for comparing a desired internal air pressure value of the inflatable chambers 170 with the actual internal air pressure, and a pressure adjusting assembly, also in operational communication with the controller, for adjusting the actual internal pressure. The controller may be activated by active feedback data derived from the comparator for maintaining a desired internal pressure value in the inflatable chambers 170 by adjusting the amount of inflation of the inflatable chamber 170 or of the groups of inflatable chambers 170, such as first and second groups of inflatable chambers 170.

The controller may be operationally connected to a first conduit and a second (or multiple) conduit and a pump for inflating the inflatable chamber 170 or plurality of inflatable chambers 170. Each inflatable chamber or plurality of chambers 170 may be independent of each other inflatable chamber 170 so that each inflatable chamber 170 may react to air pressure changes independently, or may be connected as a group and may react in concert with the air pressure changes in the other inflatable chambers 170 of the group. The air may be redistributed within the chambers 170 and the interface pressure may be maintained at any point on the top surface of each of the plurality of chambers 170 which is engaged with an anatomical portion of the user's body, at an average pressure below a capillary occlusion pressure threshold of 32 mm Hg, for example.

The total thickness of the compression sensitive switch 200 is determined by the desired distance between the patient's "most protruding part" 230 (FIGS. 8-11) and the point of "bottoming out." For example, if the desired resting distance between the most protruding part and the base of the support is ¾-1 inch, the total thickness of the stack of materials forming the compression sensitive switch 200 should be approximately 1-1¼ inch. This may consist of an upper compressible foam layer 210 that is ¼ inch thick and a compressible switch layer 206 that is ¼ thick and a lower compressible foam layer 212 that is ½-¾ inch thick. Other heights and thicknesses are anticipated.

As shown in FIGS. 8-11, the entire switch 200 assembly may be a laminated compression sensitive switch 200 advantageously encapsulated in a durable and preferably vapor resistant switch encapsulation shell 214 for added durability and protection from mechanical and chemical damage. The encapsulation material may be a coating such as silicone rubber, urethane, PVC or neoprene. A spray-on vinyl coating may be applied to the outer surface of switch 200. Alternately, the switch encapsulation shell 214 may be made of one or more layers of plastic film such as urethane or PVC, formed into a sealed shell, hermetically-sealed or otherwise. Other suitable polymeric encapsulation materials and techniques are anticipated.

As shown in FIGS. 6 and 7, the entire compression sensitive switch 200 may be located within an inflatable chamber 170. The switch 200 may be anchored into a specific position, such as at the bottom of the inflatable chamber 170. However, in some embodiments, the switch could be attached to the top of the inflatable chamber 170. The switch 200 may be bonded to the material of the inflatable chamber 170 with adhesive or by thermal bonding techniques. Alternately the switch encapsulation shell 214 may include one or more stripes of plastic film material that can be bonded to the inflatable chamber 170 material. For example, plastic film may extend from each end of the switch 200 and be bonded into the bonded seam forming the ends of the inflatable chambers 170.

In some embodiments, the controller algorithm inflates the inflatable underbody support 3 to a predetermined air pressure such as 1 psi, while the patient is being moved and positioned on the underbody support 3 (FIG. 13, Time F). Positioning the patient is facilitated by having the underbody support 3 in a relatively firm condition, preventing the patient from sinking into the underbody support as shown in FIGS. 6 and 7.

In some embodiments, the controller is then signaled, for example, by the operator pressing an operation switch, that the patient is positioned and the controller should initiate the algorithm that releases air from the inflated inflatable chambers 170. Alternately, the controller may automatically sense the positioning of the patient by a change in air pressure in the underbody support 3 caused by the patient's weight and initiate the algorithm to start. The release of air may allow the patient to sink into the underbody support 3 for maximal surface contact with the patient's skin and therefore minimal surface contact pressure with the skin (FIG. 12, Time A⇒B).

Maximal surface contact may occur just before the most protruding body part 230 (FIGS. 8-11) "bottoms out" on the hard surface below. In this position, the patient is as close to floating (as in floating in water) as can be achieved with an inflatable underbody support 3 of any given thickness. The air may be released and the patient may be allowed to sink into the underbody support until the most protruding body part 230 reaches a predetermined distance from the bottom of the most depressed inflatable chamber 170. At that point the most protruding body part 230 contacts and closes one or more switches 200 (e.g., flexible, radiolucent compression sensitive switches) (FIG. 12, Time B). This situation is also illustrated in FIGS. 8 and 9.

Figure 10:
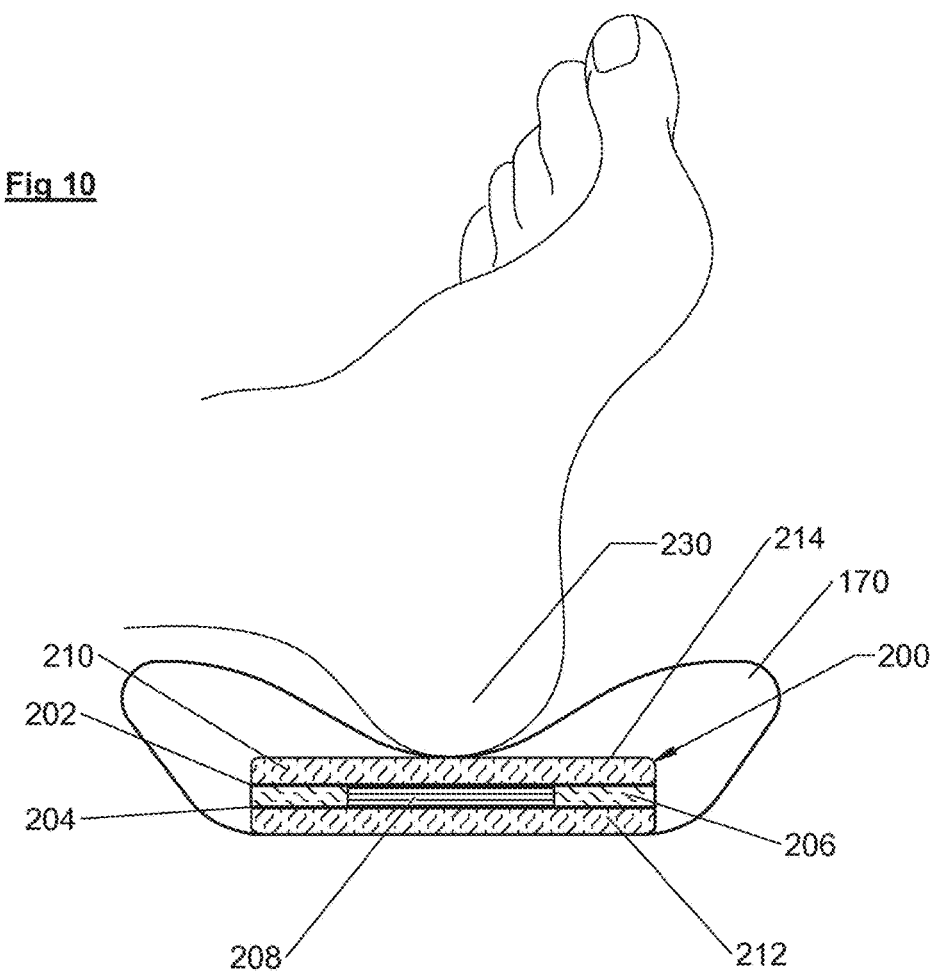
Figure 11:
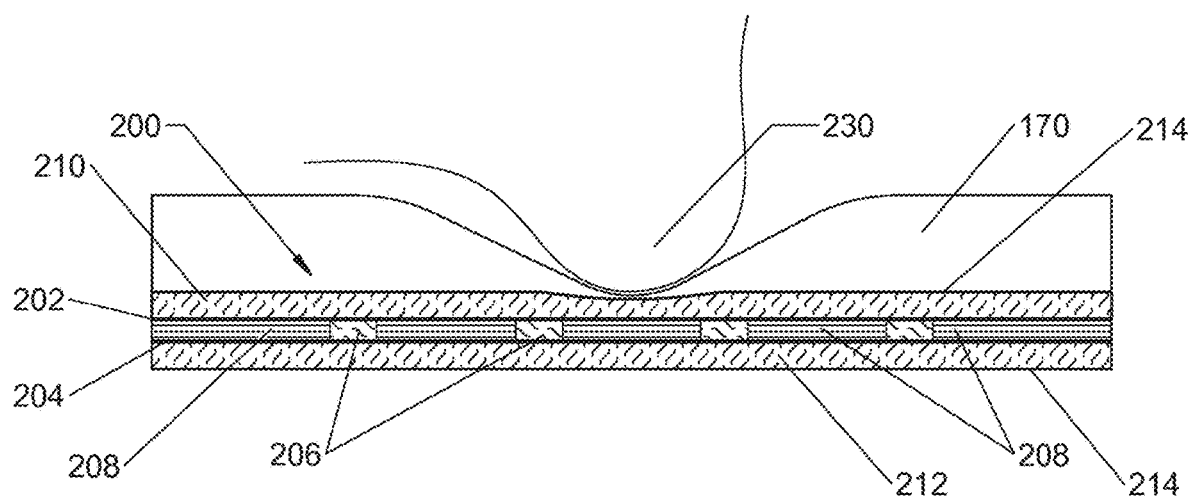

The closed switch 200 allows a small electric current to flow to the controller activating the next step in the sequence of the algorithm, which stops the air release. In some embodiments, the next sequence in the controller algorithm is then activated and it energizes the air pumps to re-inflate the inflatable chambers 170 until the most protruding body part of the patient 230 is lifted and no longer compresses the compression sensing or pressure sensing switch 200 within the most depressed inflatable chamber 170 and the electric current is no longer flowing through the switch 200 (FIG. 12, point C). This situation is also illustrated in FIGS. 10 and 11. In this position, the most protruding body part of the patient 230 is accurately positioned at a predetermined distance above hard base surface. To achieve and maintain this maximally accommodating position, the air volume within the inflatable chambers 170 must be controlled, not the air pressure.

With the compression sensitive switch 200 in the open position, it can then function as a safety sensor, detecting shifts in patient positioning or inadvertent loss of air from the inflatable chambers 170 that may result in "bottoming out." Should the switch 200 re-close during the operation (FIG. 12, point D), reestablishing the situation illustrated in FIGS. 8 and 9, the controller will sense the electrical current flow and the algorithm may automatically activate the air pumps to inflate the inflatable chambers 170 until the switch 200 once again opens and/or an alarm may be activated.

The safety sensor feature of the compression sensitive switch(es) can also be used to document that the patient did not have a body part that was inadvertently "bottomed out" for a prolonged period during the operation. This information can be automatically transmitted to the electronic medical record (EMR) for documentation. Documentation that the patient did not "bottom out" during surgery indicates that the patient was well supported and protects the surgical staff from blame should a pressure ulcer later form.

At the end of the surgical or medical procedure, the operator may once again signal the controller, such as by pressing a switch, to initiate the algorithm that energizes the air pumps to re-inflate the inflatable chambers 170 to a predetermined air pressure. The relatively firm underbody support 3 may facilitate moving the patient off of the underbody support 3.

Embodiments of the switches 200 for control of the volume of air within the inflatable chambers 170 have been disclosed. Other technologies for detecting air volume or a minimum distance/clearance between portions of the inflatable chambers 170 may alternatively be used. Other designs of switches 200, such as compression sensitive switches including different materials, different stacks of materials and different constructions may also be used. Different algorithms used to control the function of the inflatable chambers 170 in response to inputs from the volume sensors or compression sensitive switches 200 may also be used in various embodiments.

Figure 16:
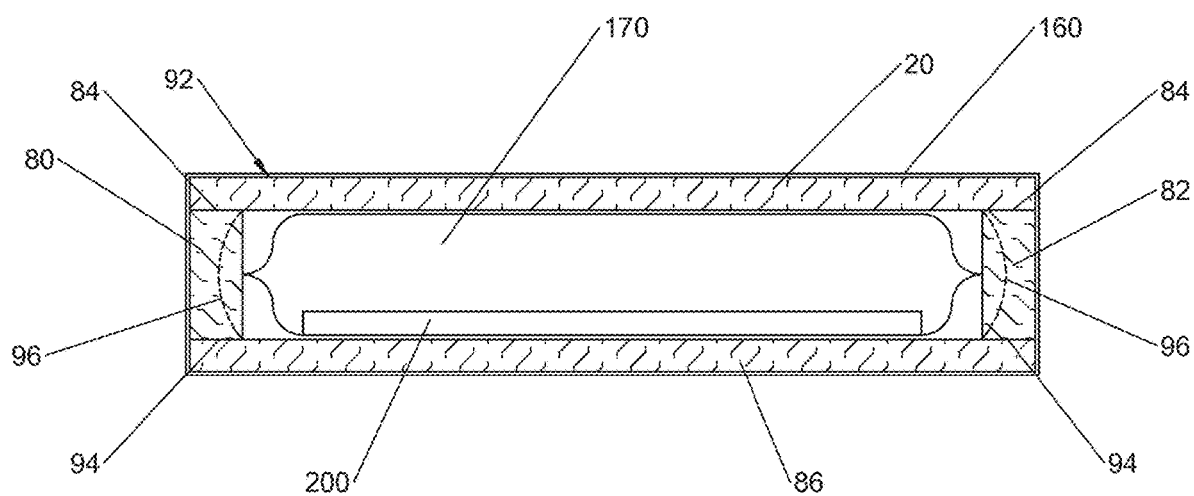
FIG. 16 is a cross-sectional view of an inflatable chamber surrounded by a box-like structure in accordance with illustrative embodiments.
Figure 17:
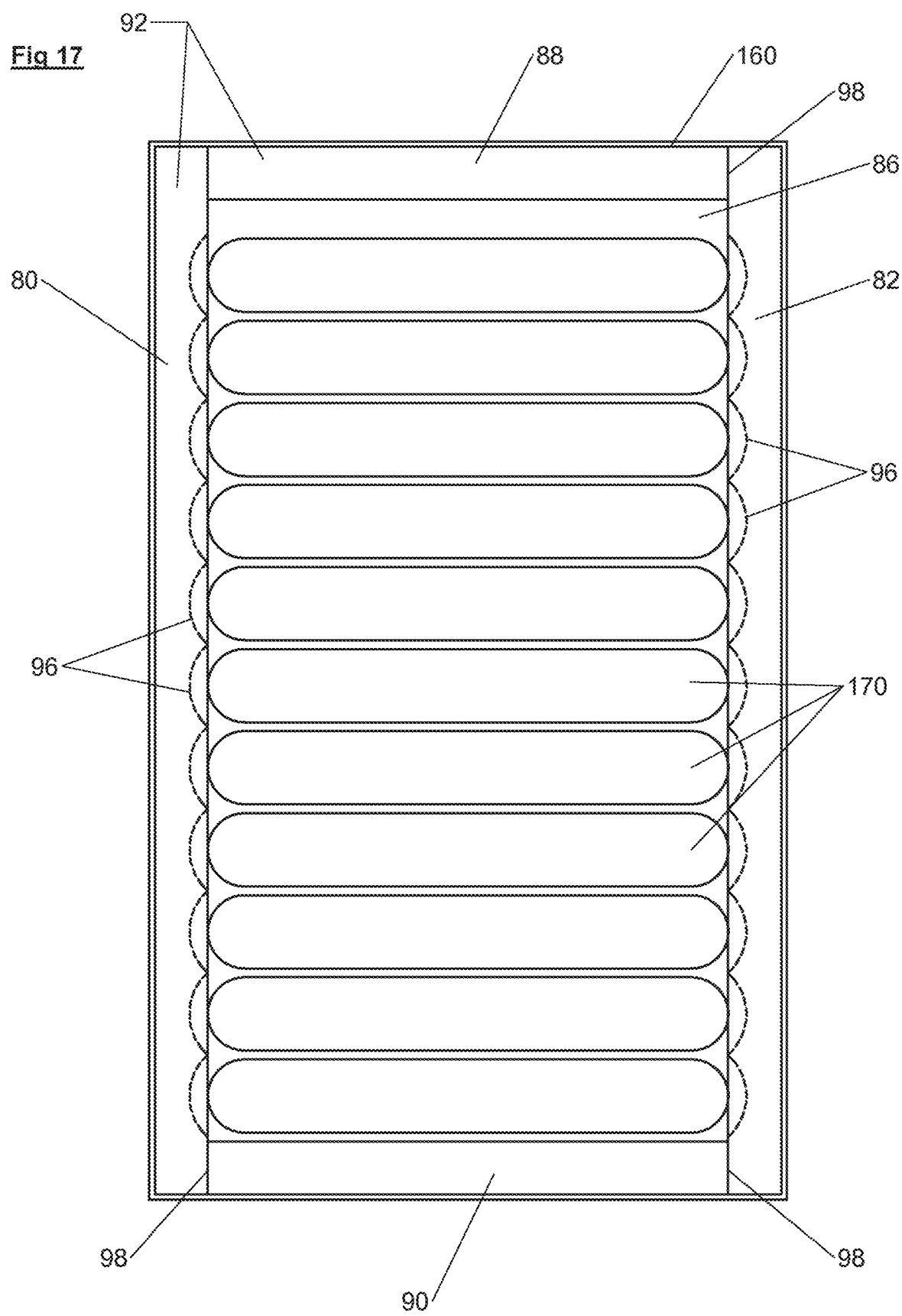
FIG. 17 is a top view of the inflatable chamber and portions of the box-like structure of FIG. 16 in accordance with illustrative embodiments.
Figure 18:
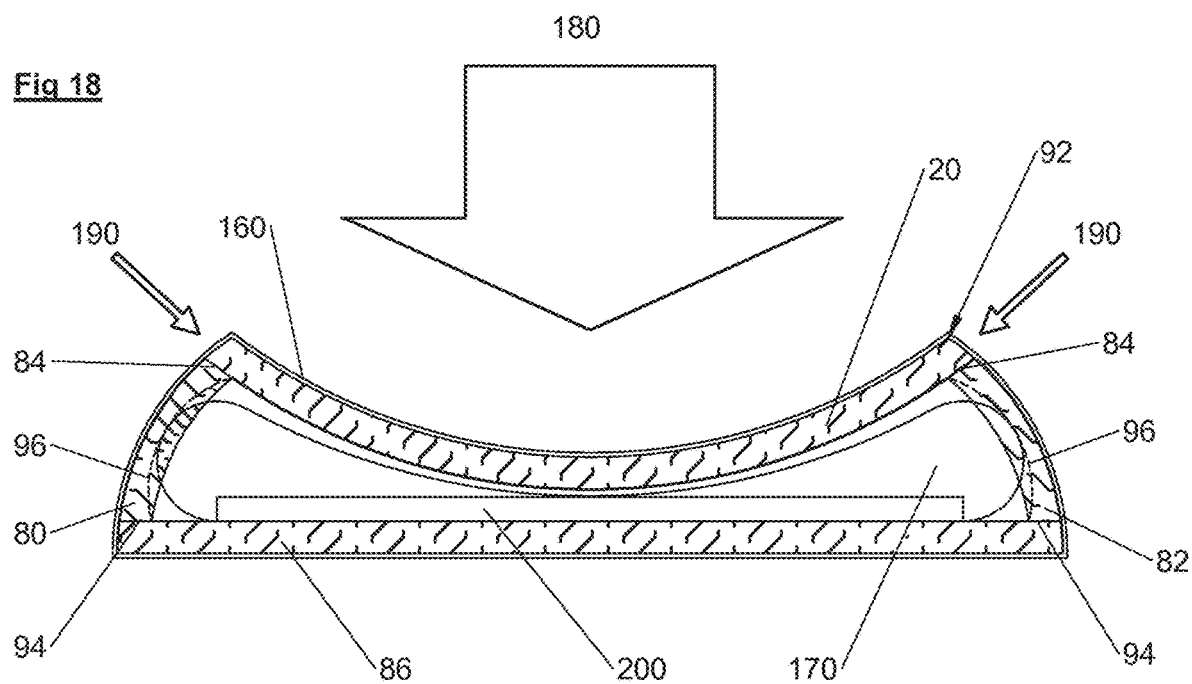
FIG. 18 is a cross-sectional view of the embodiment of the inflatable chamber and box-like structure of FIG. 17 as deformed by the weight of a patient in accordance with illustrative embodiments.

In some embodiments, the inflatable chambers 170 of the underbody support 3 include a surrounding structure that preferably may be made of foam. As shown in FIGS. 16-18, the compressible material layer 20 may be a layer of foam positioned on top of the inflatable chambers 170. Many types of foam are anticipated for this use but urethane upholstery foam that is both durable and inexpensive may be used. Two flexible side walls 80, 82 may also be made of foam and may be bonded 84 (FIG. 18) to the compressible material layer 20. Two flexible end walls 88, 90 may also be made of foam and may be bonded 84 to the compressible material layer 20 and bonded 98 (FIG. 18) to the flexible side walls 80, 82. The resulting box-like structure 92 may be open on the bottom and fit over the assembly of inflatable chambers 170, creating the external appearance of a cut foam mattress, rather than the rounded and poorly fitted look of the inflatable chambers 170. In some embodiments, the bonded joints 84 and 98 may be reinforced by bonding a layer of fabric to the foam adjacent the joints with the fabric traversing the joints for added strength.

In some embodiments, the box-like structure 92 may be made of foam and may sit on a base layer 86, also optionally made of foam. The fasteners 94 between the flexible side 80, 82 (FIG. 16), the end walls 88, 90 (FIG. 17), and the base layer 86 are preferably detachable. The fasteners 94 may be strips of Velcro hook and loop fasteners. However, other fasteners such as zippers and snaps may be used. The box-like structure 92 may be encased within a water resistant cover 160.

The box-like structure 92 of this invention may not only improve the cosmetic appearance of the underbody support 3 compared to the look of tubular inflatable chambers 170, it may also serve the function of preventing "hammocking." Hammocking occurs when the materials of the upper surface of a support or mattress cannot stretch adequately to allow the patient to optimally sink into the support. If the materials of the upper surface of the support are stretched laterally, the materials may act like a cot or hammock when the person lays on the support and prevent the person from sinking into the support. This may negate the pressure relieving purpose of the support.

In various embodiments, the flexible side walls 80, 82 and to some extent the flexible end walls 88, 90 in combination with the collapsible inflatable chambers 170, may create a tension relieving hinge shown in FIG. 18. As the inflatable chambers 170 are deflated, the person laying on the underbody support 3 sinks into the underbody support 3, depressed by the weight of the patient 180 on the upper surface. When depressed by the weight of the patient 180, the upper surface (e.g., upper surface of 160, 20, FIG. 18) pulls the materials of the upper surface of the underbody support 3 toward the center line of the underbody support 3. This would cause hammocking but for the flexible side walls 80, 82 hinging inward 190 as shown in FIG. 18, to provide strain relief for the materials of the upper surface (e.g., 160, 20 in FIG. 18).

Surgeons have been known to complain about legacy air mattresses used during surgery. Since the patient is "floating" on a cushion of air, they also tend to move when they are leaned against or pulled, as in the firm application of a surgical retractor. The lateral movement of the anesthetized patient can make the delicate sewing or cutting of the surgical procedure more challenging. Therefore, it is advantageous to have a stabilizing means in conjunction with the air mattress to prevent inadvertent lateral movements of the patient on the mattress. In various embodiments, the flexible side walls 80, 82 and to some extent the flexible end walls 88, 90 in combination with the collapsible inflatable chambers 170, may create a tension relieving hinge as shown in FIG. 18. As the inflatable chambers 170 are deflated, the person laying on the underbody support 3 mattress sinks into the underbody support 3, depressing by the weight of the patient 180, the upper surface (e.g., 160, 20 in FIG. 18). Depressing the upper surface pulls the materials of the upper surface of the support toward the center line. This causes the flexible side walls 80, 82 to hinge inward 190 as shown in FIG. 18. In this position, the top of the flexible side walls 80, 82 are moved into a position proximate the sides of the patient laying on the underbody support 3. The flexible side walls 80, 82 are relatively stiff compared to the inflatable chambers 170 and when the side walls 80, 82 abut the sides of the patient, they stabilize the patient preventing lateral movement that may be caused by the surgeon leaning or pulling the patient. By configuring the flexible side walls 80, 82 to hinge inward 190 as shown in FIG. 18, they effectively stabilize the patient from lateral movement.

Indentations 96 may advantageously be added to the inner surface of the flexible side walls 80, 82 that correspond with the rounded ends of the inflatable chambers 170. These indentations 96 in the foam flexible side walls 80, 82 create more space for the hinging action of the flexible side walls 80, 82. The hinging action that may result in strain relief for the materials of the upper surface can be achieved by creating a space in the internal region of the underbody support 3 into which the flexible side walls 80, 82 can hinge inward. This space may be created by the deflating of the volume-controlled, inflatable chambers 170. As the inflatable chambers 170 collapse to a smaller volume creating an empty space, the flexible side walls 80, 82 may hinge inwardly into the newly formed space, providing strain relief for the materials of the upper surface. Since pressure regulated inflatable chambers may not be able to safely collapse to a partial volume, inflatable mattresses with pressure control may not be able to create the hinging action and strain relief of this invention.

Figure 19:
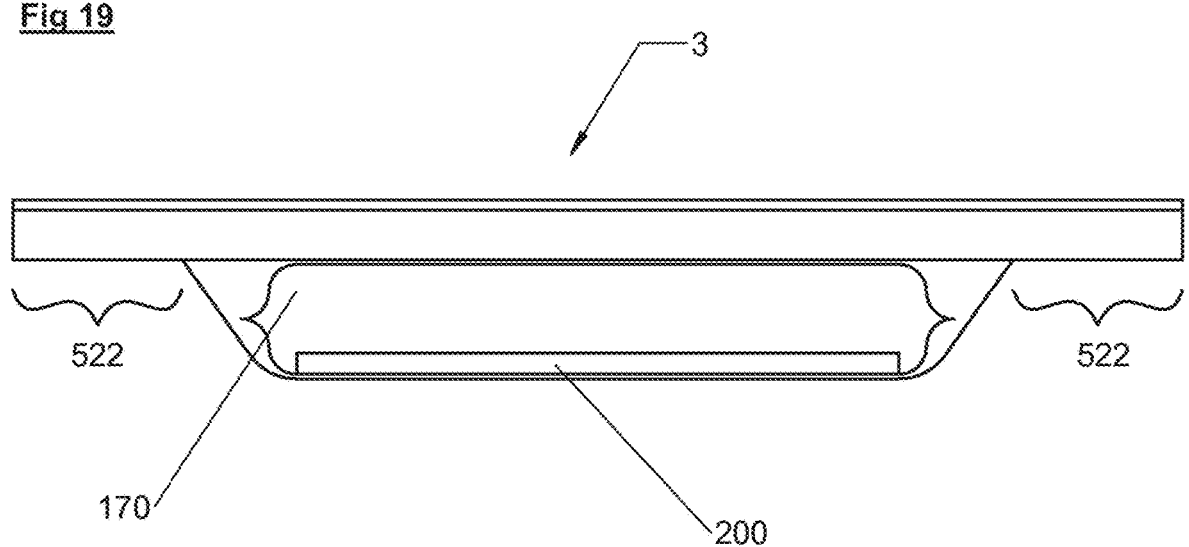
FIG. 19 is a cross-sectional view of a heater assembly overlaying an underbody support in accordance with illustrative embodiments.
Figure 20:
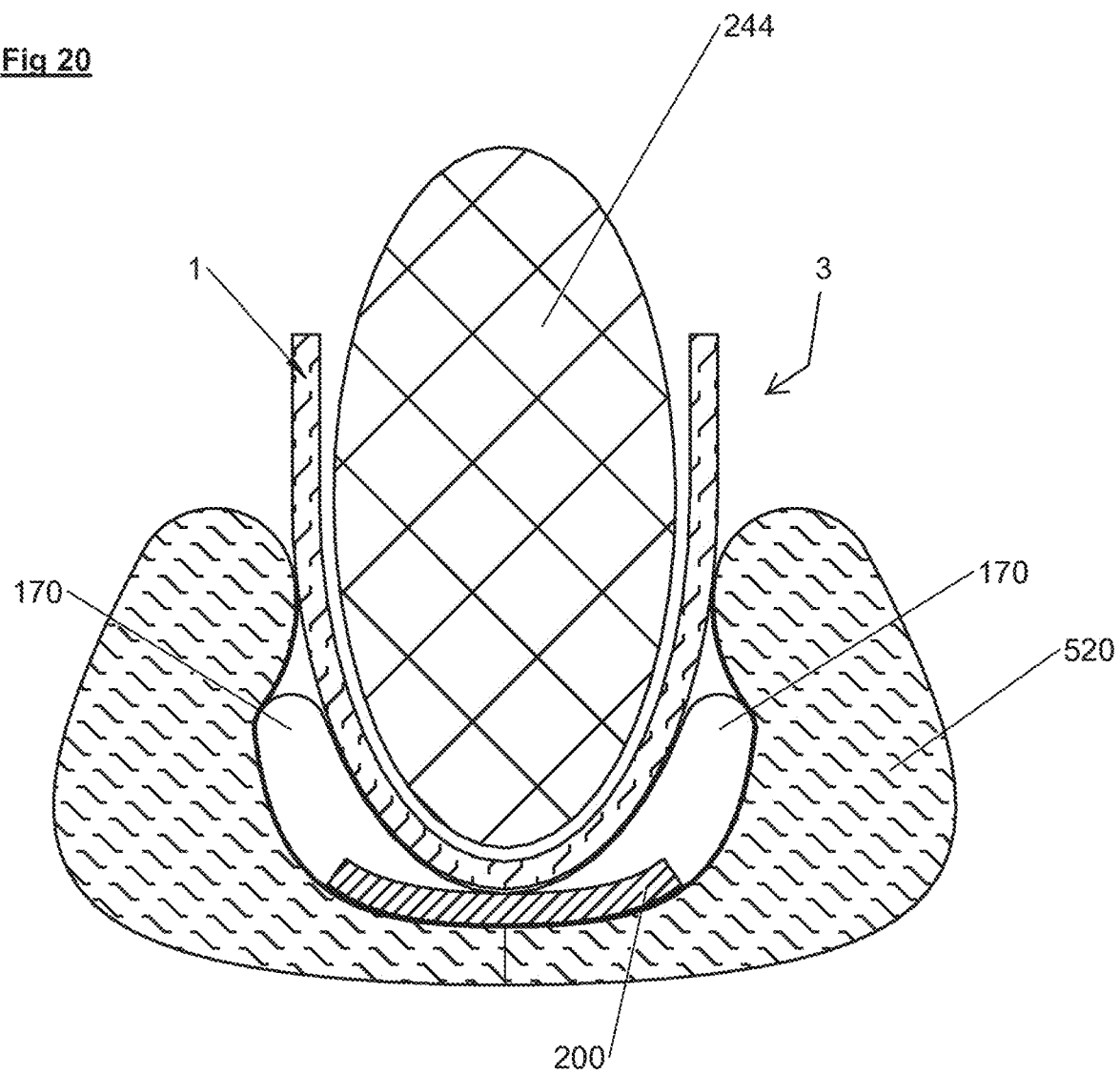
FIG. 20 is a cross section view of a heater assembly folded up against a patient's front and back side by an underbody support in accordance with illustrative embodiments.

In some embodiments as shown in FIGS. 19 and 20, the underbody support 3 may include the assembly of inflatable chambers 170 of the instant invention, advantageously combined with a heater assembly 1 (FIG. 20), for use when orthopedic surgery positioning apparatuses are used. For example, one type of positioning apparatus is a bean bag 520 (FIG. 20) which are large bags full of Styrofoam "beans" that can be put under and then formed around at least a portion of the patient (e.g., 244). A vacuum removes the air from within the bean bag 520, locking the otherwise flexible, malleable bag full of beans, into a firm shape that can be used to hold the patient in a given position such as laying on their side (lateral) 244 for hip surgery. The part of the stiffened bean bag 520 under the patient (e.g., 244) is a relatively hard, uneven, lumpy surface that can cause significant localized pressure to be applied to the patient's skin, causing pressure ulcers. Another example is the well-known peg board positioner. In this case a board with holes in it is placed on top of the mattress of the surgical table. The patient is positioned on their side (laterally) 244 and held firmly in this position by pegs (not shown) that are inserted into holes in the board and pressed firmly against the front and back sides of the patient. Lying on a hard board obviously increases the chances of pressure ulcers forming. However, the surgeons need the patients to be well-secured and stabilized, especially for operations such as hip replacements that require sawing and hammering. Padding these hard and irregular surfaces while preserving their ability to stabilize the patient, is very difficult.

In some embodiments, it is advantageous to shorten the inflatable chambers 170 (e.g., transverse inflatable chambers) so that they extend over approximately the middle ⅔ of the table width (e.g., central portion). This allows the patient who is lying on their side, to be supported by the inflatable chambers but the ends of the chambers do not interfere with the pegs of the peg board or the vertical side walls formed by the bean bag. The weight of the patient is supported by the inflatable chambers 170 but the securing function of the positioning apparatuses is not encumbered.

In some embodiments as shown in FIG. 19, the heater assembly 1 (FIG. 20) overlaying the underbody support 3, extends as lateral portions 522 beyond the ends of the transverse array of inflatable chambers 170. The flexible heater assembly 1, can be folded upward along the front and back of the laterally positioned patient (e.g., 244), without interfering with the security of the bean bag 520 or peg board. In this position, the lateral portions 522 of the heater assembly 1 are tucked between the patient and the positioning apparatus (e.g., 170, 520), which holds the heater assembly 1 against the patient's skin (e.g., 244) for optimal heat transfer.

In some embodiments, the algorithm for controlling the heated mattress overlay (e.g., 3, 1, 170, 520) during certain uses, such as orthopedic surgery, may be different than previously described. For example, it may be advantageous to have the mattress overlay (e.g., 3, 1, 170) fully deflated while positioning the patient and forming the bean bag 520 or inserting the pegs in the peg board. As shown in FIG. 20, the flexible heater assembly 1, is folded up against the patient's front and back side and held in that position by the bean bag 520 or peg board pegs.

Once the patient is positioned, the staff may start the control algorithm, which actuates the air pump(s) to inflate the inflatable chambers 170 from their collapsed condition. In the collapsed or deflated condition, the most if not all of the compression sensitive switches 200 will be in the closed position due to the weight of the patient. Air is pumped into the inflatable chambers 170 until the compression sensitive switch 200 in the most depressed chamber opens. When this last switch 200 opens, the electric current ceases flowing to the controller and the control algorithm interprets this as evidence that the patient is totally supported by air with no pressure points. No contact is occurring between the dependent, weight bearing skin of the patient and the hard surface of the bean bag 520 or peg board.

In some embodiments, the compression sensitive switches 200 in their "open" position (indicating that the patient is well supported) then may become safety sensors. If due to movement of the patient or inadvertent air loss from the system, the most protruding part of the patient contacts the bean bag 520 or peg board, the compression sensitive switch 200 at that location closes, causing the control algorithm to add more air to the inflatable chambers 170 until the compression sensitive switch 200 reopens indicating a safe condition. The control algorithm may also sound an alarm to alert the surgical staff of the patient contact. The compression sensitive switches 200 may also serve as a documentation system for safety. If the control algorithm documents that none of the compression sensitive switches 200 were closed for a prolonged period of time during any operation, it can be assumed that the patient was not subjected to prolonged pressure against the skin. The documented safe condition may be automatically charted in the electronic medical record (EMR), protecting the surgical staff from liability should a pressure ulcer develop later.

Figure 21:
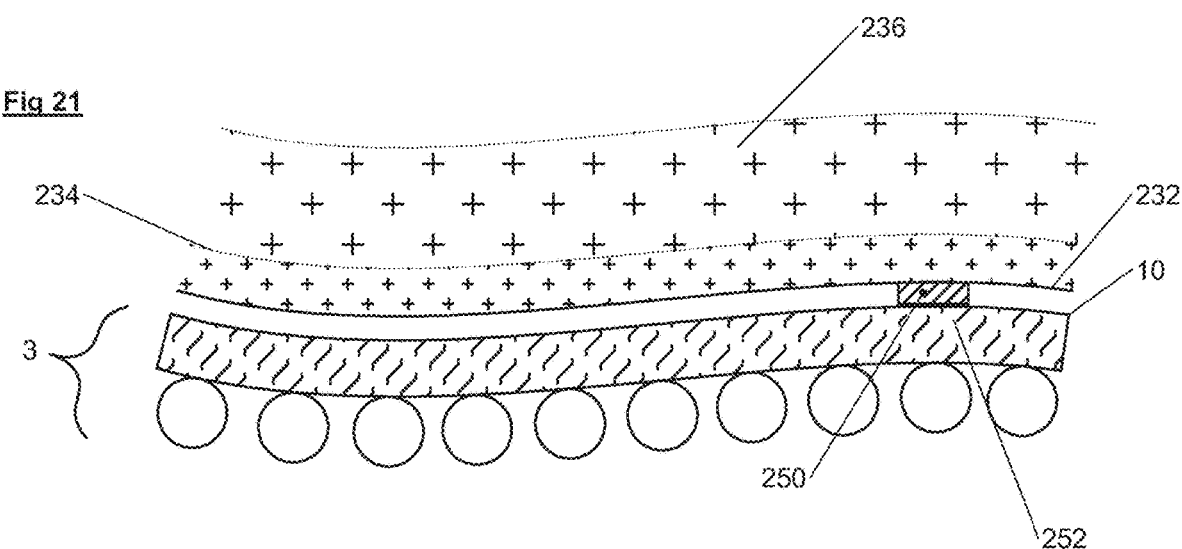
FIG. 21 is a temperature sensor interposed between a heated underbody support and a body surface of the patient in accordance with illustrative embodiments.

In some embodiments as in FIG. 21, one or more temperature sensors 250 may be arranged or configured to be interposed between the heated underbody support 3 and skin of the back or another dependent body surface of the patient 232 during a temperature measurement. The heated underbody support 3 may warm a peripheral thermal compartment 234 of the patient 230 that is in contact with the heated surface, creating a condition of near thermal equilibrium (e.g., thermal equilibrium or in substantially thermal equilibrium) between a core thermal compartment 236 and the peripheral thermal compartment 234. In this situation, the temperature of the skin of the patient that is in contact with the heated underbody support 3 accurately reflects core body temperature.

Figure 22:
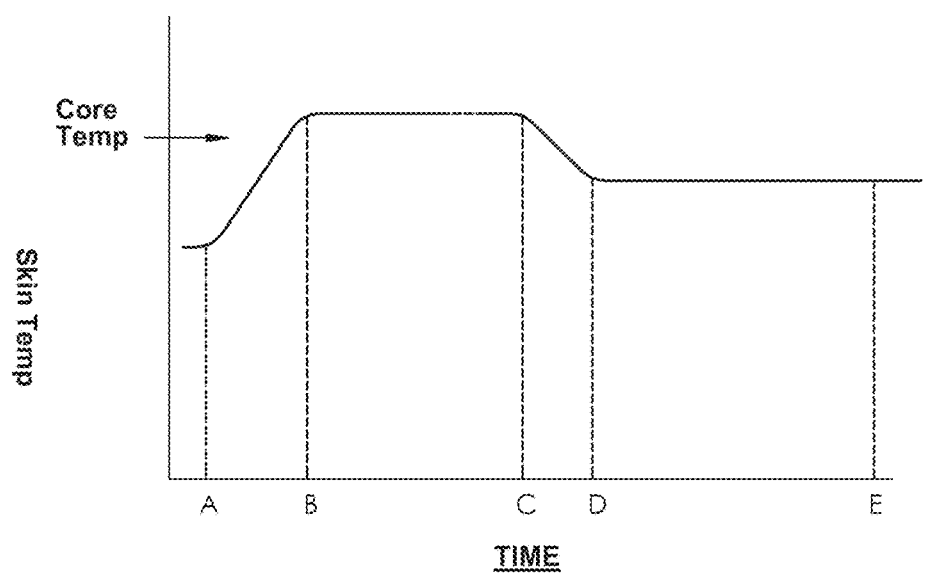
FIG. 22 is an illustrative plot of skin temperature vs. time as measured by the temperature sensor of FIG. 21 in accordance with illustrative embodiments.

This may be accomplished by sensing the core temperature using the technique described in U.S. Patent Application 2012/0238901, Non-invasive Core Temperature Sensor, filed Mar. 17, 2012, for example. In FIGS. 21 and 22, the heating element 10 of the underbody support 3 may heat the skin of the patient's back 232 to a temperature slightly greater than core (Time A⇒B) and then the temperature of the heating element 10 (e.g., a set-point temperature) may be reduced to a temperature equal or below the core temperature of the patient. When the heating element 10 temperature is reduced or turned off (Time C), a temperature sensor 250 which may be a single temperature sensor 250 contacting the body surface of the patient 232 that is interfaced with the underbody support 3, may detect the decrease in skin temperature as the excess heat from the peripheral thermal compartment 234 equilibrates by flowing into the core thermal compartment 236 (Time C⇒D). The temperature sensor 250 may be a single temperature sensor 250 and the body surface of the patient 232 may be the skin of the back of the patient.

The curve of plotted skin temperatures in FIG. 22 shows an early phase of rapid temperature reduction (Time C⇒D), followed by a phase of slow or even zero temperature reduction (Time D⇒E). The temperature at the point where the temperature curve transitions from rapid reduction to slow reduction (Time D), may correlate with the temperature at which equilibrium is reached between the peripheral and core thermal compartments 234, 236 (Time D⇒E). At equilibrium, the measured peripheral temperature can reliably correlate with core temperature. Alternately, the temperature may be recorded at a predetermined time after the heater temperature is reduced (Time E), for example between 1 and 5 minutes, when equilibrium between the peripheral compartment 234 and the core compartment 236 of the patient can be assumed to have been reached.

In some embodiments, determining when the equilibrium has been reached between the peripheral compartment 234 core compartment 236 may be determined by calculations calculated at regular intervals or on an ongoing basis rather than at a predetermined time. For example, the rate of temperature change (dT/dt) of the peripheral compartment 234 falling below a rate of temperature change threshold may be used to indicate that equilibrium has essentially been reached and the temperature may be read. In some embodiments, a comparison of a first rate of change over a first time period, to a second rate of change over a second time period falling below some value (e.g., percent change or the difference between the first rate of change and the second rate of change) may indicate that equilibrium has essentially been reached.

The temperature sensor 250 may be a thermistor or thermocouple mounted on a thermally insulating material 252, such as a disc of foam. The thermally insulating material 252 may be many sizes and shapes but may optionally be between ½-1 inch in diameter and may be ⅛-⅜ inch thick. The thermally insulating material 252 may thermally insulate the temperature sensor 250 from direct thermal contact with the heating element 10 (e.g., low mass thermal heater). The temperature sensor 250 may be placed so that it is directly contacting the body surface of the patient 232 and is thus positioned between the body surface of the patient 232 and the underbody support 3. For example, the temperature sensor 250 may be in contact with the skin of the back of the patient 232. Although any other suitable skin surface may be used. The thermally insulating material 252 that may be attached to the temperature sensor 250 may be interposed between the temperature sensor 250 and the heating element 10, minimizing the direct influence of the heating element 10 on the temperature sensor 250. In some embodiments, the one or more temperature sensors 250 are not interposed as previously described, but rather is surrounded (e.g., about its diameter), by the heated underbody support 3.

When first used, such as at the beginning of a surgical procedure, the peripheral thermal compartment 234 may be much cooler than the core thermal compartment 236 (Time A), and the temperature of the heating element 10 may be raised well above the normal safe operating temperature for a heated support, for a short time. This heats the peripheral thermal compartment 234 faster (Time A⇒B), allowing a faster initial temperature recording and more rapid onset of effective patient warming. For example, if the normal safe operating temperature for a heated underbody support 3 is 40° C., the underbody support may be initially heated to 45° C. for 5-15 minutes and then automatically reduced to the normal safe operating temperature of 40° C.

Another way to approximate core temperature utilizes the fact that the heater assembly 1 of the underbody support 3 cannot be significantly warmer than the core thermal compartment 236 and not cause thermal injuries. In this condition, if the temperature sensor 250 is in contact with the skin of the patient's back 232 and the temperature sensor 250 is thermally insulated 252 from direct contact with the heating element 10 and/or heater assembly 1, the core thermal compartment 236 temperature can be approximated once the peripheral thermal compartment 234 has been warmed and allowed to be brought into equilibrium with the core thermal compartment 236 temperature.

The temperature monitor may include a power supply switch to facilitate the steps of heating and rapid cooling of the heating element 10, and thus the heater assembly 1. For example the power supply switch can supply power to the heater assembly 1 to control the heating element 10 (e.g., low thermal mass heater) to a temperature that is greater than core thermal compartment temperature 236. Then the heating element 10 temperature rapidly reduces to a temperature that is less than the core body temperature 236 when the power supply switch cuts off power to the heating element 10. It may be preferable to discontinue power to the heating element 10, however, in some embodiments, the power may be substantially discontinued rather than completely discontinued. For example, the power may be reduced by 90%, or the cycle time between power supplies may be reduced by 90%.

An alternative way which may be used to determine core temperature is for the temperature monitor to have two temperature sensors (e.g., 250) separated by a small piece of thermal insulation, in a construction known as a "heat-flux transducer," for example. The first temperature sensor 250 in contact with the body surface of the patient 232 may reflect the patient's temperature and the second temperature sensor (not shown) in contact with the heating element 10 may reflect the heating element 10 temperature. The heating element 10 temperature may then adjust until the two temperature sensors equal each other and reach equilibrium. At that point there may be zero heat flow (heat flux) and the patient's core temperature may be equal to the skin temperature. This technique may reduce the heating effectiveness of the surface of the heater assembly 1, but it will allow continuous temperature monitoring.

Various temperature monitoring techniques described herein use the heating element 10 of the underbody support 3 to equilibrate the temperature of peripheral thermal compartment 234 with the temperature of the core thermal compartment 236. These temperature monitoring techniques may also efficiently use the heating element 10 and underbody support 3 itself as the thermal insulation between the patient and the environment.

The temperature monitoring techniques of the instant invention may rely on excess heat being added to the peripheral thermal compartment 234. The excess heat may then be allowed to flow into the cooler core thermal compartment 236 (Time C⇒D) until thermal equilibrium is reached (Time D⇒E). This is different than all other core body temperature monitors that attempt to measure the temperature of the heat flowing out from the core thermal compartment 236 to the peripheral thermal compartment 234 and then to the skin (e.g., 232).

In some embodiments, the underbody support 3 includes a grounding electrode for electro-surgical equipment. As shown in FIGS. 2-4, the grounding can be accomplished by placing an electrode 254 under the patient but not in direct electrical contact with the patient. Electrode 254 may be a large electrode. This can create a condition of capacitive coupling for grounding the RF electrical current without actually touching the patient. These capacitive coupling grounding electrodes 254 are well known in the art. For example, U.S. Pat. Nos. 6,053,910 and 6,214,000 describe embodiments which may be used. However, these capacitive coupling electrodes have been generally utilized as mattress overlays which are inconvenient and require extra cleaning. Further, these electrodes may be embedded into a gel pad, resulting in an overlay that is heavy, cumbersome and interferes with optimal pressure off-loading.

To avoid these problems, various embodiments include capacitive coupling grounding electrode 254 in the stack construction of the underbody support 3. The preferred location for the capacitive coupling electrode 254 in the stack is under the compressible material layer 20; however, other locations are anticipated. The electrode 254 may include or consist of a sheet of flexible and preferably stretchable electrically conductive fabric that extends substantially across the entire area of the underbody support 3. The stretchable fabrics may be woven twills or knits, for example. If a non-stretchable or less stretchable fabric such as woven nylon or polyester is chosen, care must be taken in the design to avoid anchoring the non-stretchable fabric to the periphery of the underbody support 3 in order to prevent "hammocking." Various methods of preventing hammocking have been discussed in other applications already incorporated herein.

The electrode 254 may be a conductive fabric electrode that may be coated with silicone rubber, as described in U.S. Provisional Patent Application 61/812,987, to prevent electrical contact with the other electrically conducting components while maintaining optimal flexibility and stretchability. In some embodiments, the conductive fabric grounding electrode 254 may be the heating element 10 (e.g., conductive fabric heater material, fabric or film). Proper grounding of the heater material (e.g., heating element 10) may provide electrosurgical capacitive grounding without the need for an additional layer of conductive material.

To clean and sanitize medical equipment, hydrogen peroxide ($H_2O_2$) disinfecting solutions have recently been introduced into the operating room and hospital. $H_2O_2$ is a well-known, powerful oxidizing agent that kills bacteria and viruses in a mechanical way that cannot lead to resistant strains. The oxidation reaction causes the $H_2O_2$ to break down into water and oxygen, two harmless, or less harmless by-products. The problem is that $H_2O_2$ vapor is also highly oxidizing for electrical components, including flexible heater materials (including polypyrrole), metal bus bars and conductive metal coatings such as silver on fabric or thread. There is a need for better protection of the sensitive electrical components from oxidation by $H_2O_2$ and other oxidizers.

In some embodiments, urethane film may be used as the shell 42, 44 material for the underbody support 3 or related blankets, because of its strength, flexibility durability and response to heat sealing. Unfortunately, although urethane film may be good for providing a water-resistant and encapsulating shell 42, 44, urethane film is relatively permeable to hydrogen peroxide vapors, allowing the highly oxidizing vapors to enter the underbody support 3 or a related heated electric blanket. Once inside, the peroxide vapors attack any oxidizable material. These vapors can cause oxidation and failure of electrical components, especially polypyrrole. Other plastic films such as PVC are much less permeable to peroxide vapor than urethane. Since peroxide is becoming more and more common as a disinfectant for operating room and other hospital use, a way of protecting vulnerable internal components from oxidation due to peroxide is needed.

In some embodiments, the underbody support 3 or the related heated electric blankets incorporate certain materials that can protect the polypyrrole heater (e.g., heating element 10) and other oxidizable electrical components from oxidizing agents such as hydrogen peroxide ($H_2O_2$) disinfecting solutions. In some embodiments, a catalyst to accelerate hydrogen peroxide decomposition may be coated on or impregnated into an element within the shell 42, 44, or on the interior surface of the shell 42, 44.

In some embodiments, sacrificial materials may be included in the internal construction that can be preferentially oxidized. Sacrificial materials may be organic materials such as cellulose. For example, sacrificial materials such as one or more sacrificial layers 256 of cotton, linen or paper, as shown in FIGS. 2-4, may be added to the inside of the underbody support 3 or the related heated electric blanket so that the peroxide vapors preferentially attack and oxidize the sacrificial material. Other oxidizable sacrificial materials may be used. In the process of oxidizing these sacrificial materials, the peroxide breaks down into inert (e.g., less corrosive, less problematic) water and oxygen before it can attack the electrical components. The catalyst for accelerating hydrogen peroxide decomposition may decompose all, substantially all, or the majority of the hydrogen peroxide vapors before they reach the electrical components, depending on how the catalyst is incorporated into the particular apparatus.

In some embodiments, materials that are known to be catalysts for the breakdown reaction of peroxide to water and oxygen may be added. For example, manganese dioxide ($MnO_2$) powder may be added to one or more of the sacrificial layers 256 in FIGS. 2-4, or the compressible material layer 20, the inside surface of the shell 42, 44, or adhered directly to any suitable component of the heater assembly 3 by an applied coating, by impregnation into, by adhesive, or by any other suitable process.

In some embodiments, the insoluble manganese dioxide powder may be suspended in water and the sacrificial layer 256 of fabric or foam can be dipped in this water/manganese dioxide powder suspension to evenly disperse the powder throughout the sacrificial layer 256 of fabric or foam when the water evaporates. In some embodiments, a small amount of methyl cellulose can be added to the water/manganese dioxide powder suspension in order to increase the duration of the suspension time of the powder in water. The small amount, or sufficient amount of methyl cellulose to increase the viscosity of the water and manganese dioxide suspension to between 10 and 120 centipoise. The methyl cellulose may also act as a binding agent, improving adherence of the manganese dioxide powder to the fabric, foam or other material. Other binding agents, and/or suspension improvers besides methyl cellulose may be used. Adding too much binding agent (e.g., greater than 120 centipoise) can cause the binding agent to completely encapsulate the manganese dioxide powder when it dries, and too little (e.g., less than 10 centipoise) will not hold the powder in suspension very long. Other carriers besides water may also be used.

In some embodiments, the one or more sacrificial layers 256 of manganese dioxide impregnated fabric or compressible material layer 20 may be added to the inside of the underbody support 3 or related heated electric blanket so that the catalyst can preferentially attack the peroxide vapors and neutralize them to water and oxygen, before they can damage the electrical components. Other liquids are anticipated for suspending the manganese dioxide powder. Examples of catalysts that can be used in place of manganese dioxide powder include: silver, platinum and transition metal salts. Other catalysts may also be used. In some embodiments the catalysts may be added to another feature of the underbody support 3 or the related heated electric blanket, and to a material other than fabric or foam.

The effectiveness of these measures for preventing the oxidation and degradation of the heater fabric and other mattress or blanket components by peroxide vapor were tested. During testing similar squares of heater material with bus bars attached were sealed into shells of urethane film. The heaters were then placed into a chamber that continuously exposes the shell to peroxide vapor. Over the course of 9-12 days, the change in resistance of the heater material was measured and correlated with the degradation of the conductance of the heater material. Over the course of 9 days of exposure to peroxide vapor, the resistance of unprotected polypyrrole heater material increased from 58.4 to 238.2 ohms on the square. The significant increase in resistance, indicates that the conductivity of the unprotected conductive heater material (e.g., heating element 10) was rapidly degraded by the peroxide vapors.

Over the course of 12 days of exposure to peroxide vapor, the resistance of heaters that included two layers of sacrificial cotton fabric inside the shell, increased from 53.5 to 84.8 ohms on the square. Over the course of 12 days of exposure to peroxide vapor, the resistance of heaters that included two layers of polyester fabric impregnated with manganese dioxide inside the shell, did not increase resistance at all (52.8 to 52.8 ohms on the square). The $MnO_2$ was very effective as a catalyst neutralizing the peroxide vapor before it could destroy the heater. The sacrificial layer of cotton fabric was also quite effective in protecting the heater but less so than the $MnO_2$.

This disclosure of using $MnO_2$ or sacrificial cellulose layers to protect oxidizable components, especially electrical components, is not limited to underbody supports 3 and heating blankets. In some embodiments, other medical equipment (e.g., apparatus) including electrical components such as patient monitors, patient monitoring electrodes, patient monitoring sensors and medical equipment control circuits may be protected from oxidation and damage by peroxide vapors or liquid, by incorporating $MnO_2$ or sacrificial cellulose layers into the equipment, as disclosed in this application.

In some embodiments, the underbody support 3 uses the fact that the patient sinks into the underbody support 3 and achieves maximal body surface contact with the underbody support 3, to aid in preventing the patient from sliding off of the surgical table 412 when placed in the steep Trendelenburg position (head down). This is in contrast to a traditional mattress wherein the torso of the patient may only contact the mattress at the buttocks and shoulders. This relatively small contact area means that the coefficient of friction must be much greater in order to prevent the patient from slipping off of the mattress when placed in the Trendelenburg position. Various embodiments allow contact with the entire back of the patient and curve up along their sides allowing a much lower coefficient of friction to prevent slipping.

The underbody support 3 may include elements for anchoring the support to the surgical table 412. In some embodiments, the elements for anchoring may be a Velcro attachment between the upper surface of the surgical table 412 and the lower surface of the underbody support 3. In some embodiments, the elements for anchoring may be a strap attachment between the side of the surgical table 412 and the underbody support 3. The lower surface may also be called the table interface surface.

In some embodiments, a sheet of fabric that has been at least partially coated on both sides with high-friction plastic or rubber, or a material having similar characteristics, may be interposed between the patient and the support in order to increase the coefficient of friction. An example of this may be PVC or silicone that may be applied as a three dimensional pattern or three dimensional raised dots, onto a fabric (e.g., friction enhancing elements). The high-friction plastic or rubber that may be in the form of a pattern or dots, "grip" the upper surface of the underbody support 3 on one side and the back of the patient on their other side, dramatically increasing the coefficient of friction between the patient and the underbody support 3 surface, preventing the two from slipping against each other. Alternately, the high-friction plastic or rubber forming a pattern or dots may be applied directly to the upper surface of the underbody support 3. The upper surface may also be called a patient interface surface.

In some embodiments, a method of supporting and restricting a sliding motion of a patient on a surgical table including the features described previously herein includes (i) providing an underbody support configured to support the patient on the table, the underbody support including a compressible material layer having an upper surface configured to face the patient opposite a base layer having a lower surface configured to face the surgical table; (ii) coupling the underbody support to the surgical table; (iii) placing a layer of material between the upper surface of the underbody support and the patient, the layer of material comprising friction enhancing elements on both sides of the layer of material, wherein the layer of material is configured to grip both the underbody support and the patient to prevent the patient from inadvertently slipping off the underbody support; and (iv) positioning the patient on the underbody support.

In some embodiments of the method, the layer of material may be a draw sheet that is configured to be positioned over the underbody support for lifting the patient. In some embodiments the layer of material including friction enhancing elements includes PVC or silicone.

In some embodiments of the method, positioning the patient on the underbody support comprises positioning the patient in the head down Trendelenburg position, the friction enhancing elements being configured to reduce sliding of the patient relative to the underbody support when the patient is positioned on the underbody support in the head down Trendelenburg position.

In some embodiments of the method, the underbody support includes two side walls; two end walls; a base layer having a lower surface configured to face the table and a base layer perimeter; the compressible material layer may have a compressible material layer perimeter, the compressible material layer bonded to the two side walls and to the two end walls about the perimeter of the compressible material layer; and one or more inflatable chambers, wherein the two side walls and two end walls are fastened to the perimeter of the base layer, and the base layer, the two side walls, the two end walls, and the compressible material layer form a box-like structure made of flexible foam. In some embodiments the box-like structure surrounds the one or more inflatable chambers.

In some embodiments of the method, the upper edges of the two flexible side walls can hinge inward in response to the weight of a patient depressing the central region of the layer of compressible material, and the hinging inward of the flexible side walls allows the layer of compressible material to deform maximally while accommodating the patient without creating a hammock effect.

In some embodiments of the method, the upper edges of the two flexible side walls can hinge inward in response to the weight of a patient depressing the central region of the layer of compressible material, and the hinging inward of the flexible side walls allows the tops of the flexible side walls to substantially abut the sides of the patient stabilizing the patient against inadvertent lateral movement.

In some embodiments of the method, the method may further include: placing the patient in the head down Trendelenburg position, and fastening shoulder straps that extend from a head end portion of the underbody support over the shoulders of the patient to a central portion of the underbody support or the surgical table when the patient is in the head down Trendelenburg position to secure the patient to the surgical table.

Figure 23:
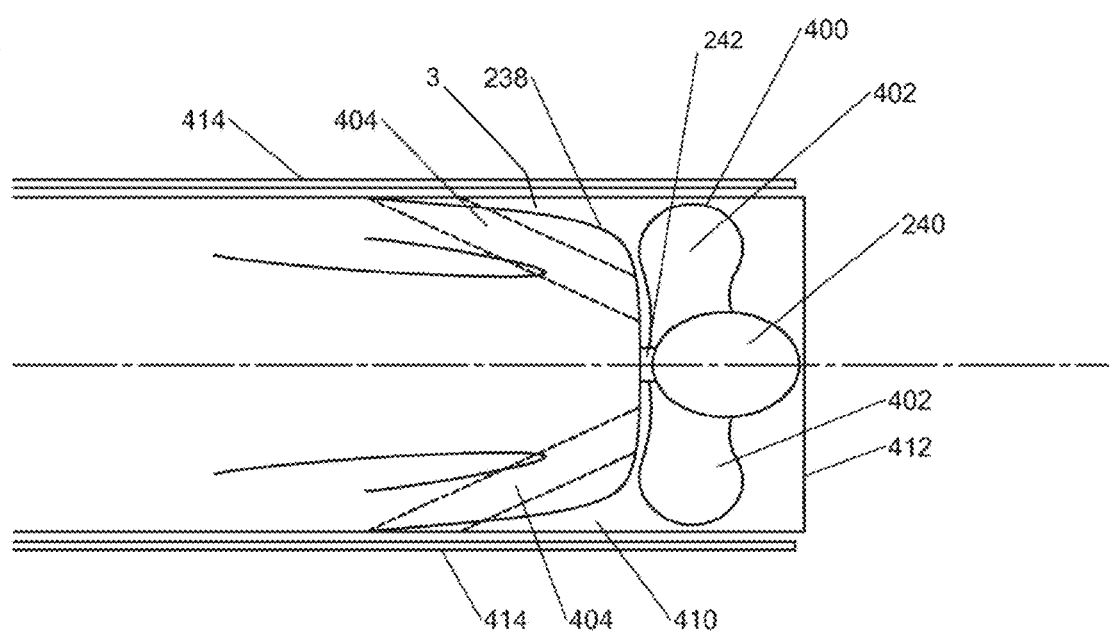
FIG. 23. is a top view of patient anchoring support features in accordance with illustrative embodiments.
Figure 24:
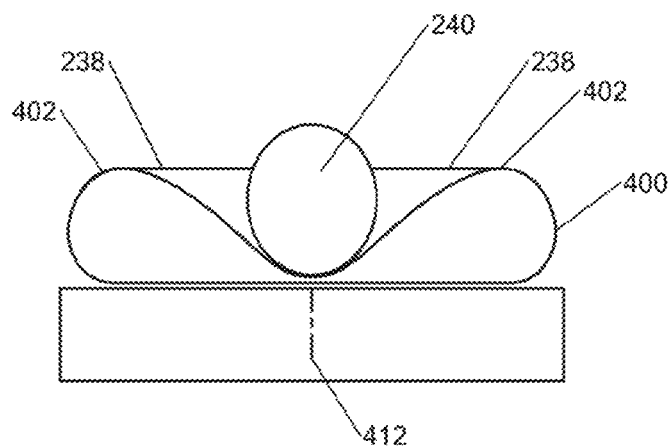
FIG. 24. is a cross-sectional view of an embodiment the patient anchoring support features of FIG. 23 in accordance with illustrative embodiments.

In some embodiments as shown in FIGS. 23 and 24, a cushion 400 (e.g., foam cushion) may be anchored to the head end of the support surface 410 and extend onto the mattress portion at the head end of the surgical table 412. The cushion 400 may optionally be substantially yoke-shaped extending transversely across the surgical table 412, with a depression in the middle to accommodate a patient's head 240 and neck 242 and with raised lateral portions 402 to engage the patient's shoulders 238. The raised lateral portions 402 interface with a patient's shoulders 238, to effectively prevent the patient from slipping off of the head end of the surgical table 412. Other cushion shapes may also be used. The cushion 400 may be formed of foam or any other suitable material.

In some embodiments, the yoke-shaped cushion 400 may also include shoulder straps 404, much like the shoulder straps of a backpack, may extend substantially from a yoke-shaped cushion 400 over the front of the patient's shoulders 238 and anchor on side rails 414 of the surgical table 412 or other surface. For example, at a central portion of the underbody support 3. Other strap configurations may be used for anchoring the yoke-shaped cushion 400 to the side rails 414 of the surgical table 412. The anchoring shoulder straps 404 may be adjusted in length as well as anchored at different locations along the side of the surgical table 412, or another part of the surgical table 412 allowing the patient to be repositioned along the surgical table 412 if necessary. In some embodiments, the yoke-shaped cushion 400 may be attached to and anchored to the head end of the underbody support 410. In some embodiments, the yoke-shaped cushion 400 may also include one or more cushion inflatable chambers to minimize point pressure on the patient's shoulders 238. The cushion inflatable chambers of the yoke-shaped cushion 400 may be similar or different to inflatable chambers 170 previously disclosed.

Figure 25:
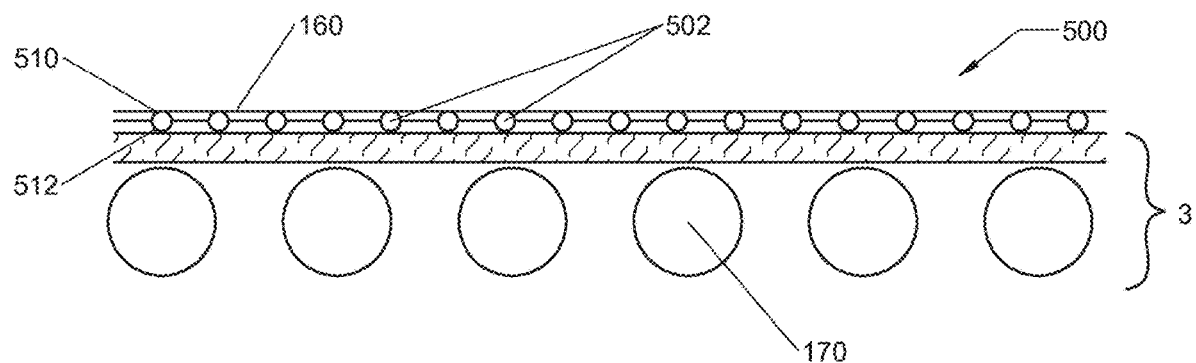
FIGS. 25-27. are cross-sectional views of a layer of water-circulating channels in accordance with illustrative embodiments.
Figure 26:
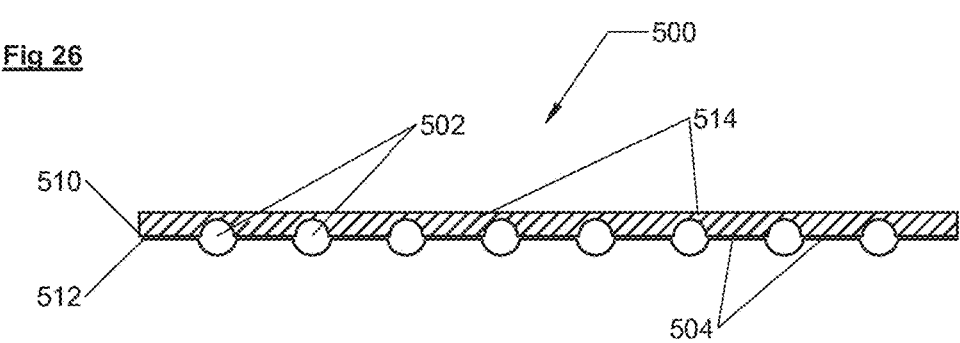
Figure 27:
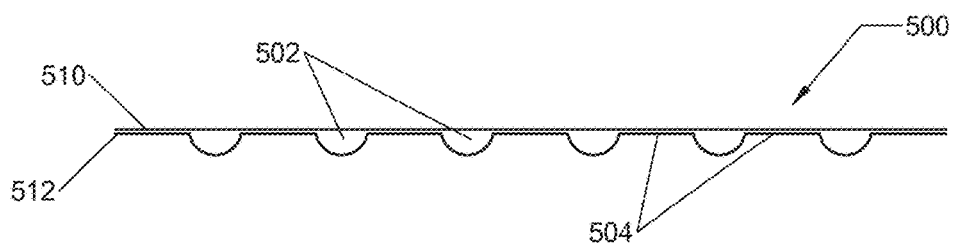

In some embodiments as shown in FIGS. 25-27, the underbody support 3 includes a layer of water-circulating channels 500 that optionally cover substantially the entire surface area of the underbody support 3. The layer of water-circulating channels 500 may be located near the patient surface of the underbody support 3, or the yoke-shaped cushion 400, including the raised lateral portions 402. Cold water may optionally be circulated through water-circulating channels 502 for inducing therapeutic hypothermia. Hypothermia has been shown to be neuro-protective for: closed head injuries; post successful CPR for heart attacks and for some strokes. Therapeutic cooling has is also useful for heat stroke and certain hypermetabolic states like malignant hyperthermia.

The water-circulating channels 502 may be molded into the two film layers 510, 512 of polymeric film that are then sealed together 504 (e.g., hermetically sealed) between the water-circulating channels 502. This construction of a layer of water-circulating channels 502 may be done according to methods known in the art. Relatively thick PVC or urethane film may be used for this purpose. The sealed portions 504 may be created using RF, ultrasound, heat, or any other suitable method of sealing. This construction results in a flexible layer of water-circulating channels 500 that can be positioned near the upper surface of the underbody support 3. Since the film layers 510, 512 forming the water-circulating channels 502 are relatively thick, they may also be relatively resistant to collapse from supporting the weight of a patient.

In some embodiments, longitudinal slits are made through the sealed portions 504 of the layer of water-circulating channels 500. These longitudinal slits allow lateral expansion of the layer of water-circulating channels as the layer is deformed by the weight of a patient. The lateral expansion of the layer of water-circulating channels 500 due to the slits may facilitate the accommodation of the patient into the underbody support 3, while preventing "hammocking."

An advantage of adding a layer of water-circulating channels 500 to the inflatable underbody support 3 of various embodiments is that the patient sinks further into this underbody support 3 than into a foam mattress, for example. By sinking into the underbody support 3, the underbody support 3 may curve up along side the patient forcing the water-circulating channels 500 into close opposition to the patient's skin over a much larger surface area than can be accomplished with a foam mattress. The greater surface area in contact with the cold water-circulating channels 500 results in more effective heat or cold transfer. Therefore, the combination of the maximally accommodating underbody support 3 of various embodiments with a layer of water-circulating channels 500 is both unique and advantageous.

In some embodiments as shown in FIG. 26, the upper surface of the layer of water-circulating channels 500 may have a coating of gel 514 to fill in the uneven surface created by the molded channels. The gel coating produces a relatively smooth upper surface for contacting the patient while maintaining thermal conductivity. Alternately, in some embodiments as shown in FIG. 27, the molded channels are only molded into the lower film layer 512 of polymeric film. This leaves the upper film layer 510 of polymeric film smooth for optimal contact with the patient.

Whereas particular embodiments of the invention have been described for the purposes of illustration, it will be evident to those skilled in the art that numerous variations of the details may be made without departing from the invention as set forth in the embodiments described herein.

The invention claimed is:

1. A heated patient securing system for use during surgery, comprising:
- an underbody support configured to support a patient, wherein the underbody support is heated, wherein the underbody support comprises a heating element, an upper shell, and a lower shell, wherein the upper shell and the lower shell encase the heating element; and
- a patient securing overlay comprising a sheet of fabric, the sheet of fabric having an upper surface configured to face the patient and a lower surface configured to face an upper surface of the underbody support;
- the sheet of fabric being partially coated on both the upper surface and the lower surface thereof with three-dimensional friction enhancing elements, the three-dimensional friction enhancing elements comprising a three-dimensional raised pattern or three-dimensional raised dots, the three-dimensional friction enhancing elements comprising plastic or rubber;
- the three-dimensional friction enhancing elements being oriented such that the three-dimensional raised pattern or three-dimensional raised dots on the lower surface of the sheet of fabric are configured to grip the upper surface of the underbody support and the three-dimensional raised pattern or three-dimensional raised dots on the upper surface of the sheet of fabric are configured to grip a back of the patient;
- the three-dimensional friction enhancing elements forming a raised pattern or raised dots on both the upper and lower surfaces of the sheet of fabric such that the partially coated sheet of fabric is uncoated on both the upper and lower surfaces thereof in areas between the raised pattern or raised dots.

2. The heated patient securing system of claim 1, wherein the three-dimensional friction enhancing elements on the upper surface of the sheet of fabric are configured to grip the back of the patient so as to increase a coefficient of friction between the patient and the patient securing overlay.

3. The heated patient securing system of claim 1, wherein the three-dimensional friction enhancing elements include a PVC material.

4. The heated patient securing system of claim 1, wherein the three-dimensional friction enhancing elements include a silicone material.

5. The heated patient securing system of claim 1, wherein the three-dimensional friction enhancing elements on the lower surface of the sheet of fabric are configured to grip the upper surface of the underbody support so as to increase a coefficient of friction between the underbody support and the patient securing overlay.

6. The heated patient securing system of claim 1, wherein the sheet of fabric partially coated with the three-dimensional friction enhancing elements is configured to be placed on the upper surface of the underbody support such that the sheet of fabric is configured to grip the underbody support.

7. The heated patient securing system of claim 6, wherein the underbody support is anchored to a surgical table by a Velcro attachment between an upper surface of the surgical table and a lower surface of the underbody support.

8. The heated patient securing system of claim 6, wherein the underbody support is anchored to a surgical table by a strap attachment between a side of the surgical table and the underbody support.

9. A method of restricting a sliding motion of a patient on a heated underbody support during surgery, comprising:
- providing a surgical table and a heated underbody support configured to support a patient on the surgical table, wherein the heated underbody support comprises a heating element, an upper shell, and a lower shell, wherein the upper shell and the lower shell encase the heating element;
- coupling the heated underbody support to the surgical table;
- placing a patient securing overlay on an upper surface of the heated underbody support, the patient securing overlay comprising a sheet of fabric that is configured to be positioned on the upper surface of the heated underbody support between the upper surface of the heated underbody support and the patient, the sheet of fabric comprising an upper surface and a lower surface;
- the sheet of fabric being partially coated on both the upper surface and the lower surface thereof with three-dimensional friction enhancing elements, the three-dimensional friction enhancing elements comprising a three-dimensional raised pattern or three-dimensional raised dots, the three-dimensional friction enhancing elements comprising plastic or rubber, the three-dimensional friction enhancing elements being configured to prevent the patient from inadvertently slipping off of the heated underbody support;
- the three-dimensional friction enhancing elements being oriented such that the three-dimensional raised pattern or three-dimensional raised dots on the lower surface of the sheet of fabric are configured to grip the upper surface of the heated underbody support and the three-dimensional raised pattern or three-dimensional raised dots on the upper surface of the sheet are configured to grip a back of the patient;
- the three-dimensional friction enhancing elements forming a raised pattern or raised dots on both the upper and lower surfaces of the sheet of fabric such that the partially coated sheet of fabric is uncoated on both the upper and lower surfaces thereof in areas between the raised pattern or raised dots;
- positioning the patient on the sheet of fabric and the heated underbody support.

10. The method of claim 9, wherein the heated underbody support is anchored to the surgical table by a strap attachment between a side of the surgical table and the heated underbody support.

11. The method of claim 9, further comprising:
- gripping the back of the patient via the three-dimensional friction enhancing elements so as to increase a coefficient of friction between the patient and the patient securing overlay; and
- gripping the upper surface of the heated underbody support via the three-dimensional friction enhancing elements so as to increase a coefficient of friction between the heated underbody support and the patient securing overlay.

12. The method of claim 9, wherein the three-dimensional friction enhancing elements include a PVC material.

13. The method of claim 9, wherein the three-dimensional friction enhancing elements include a silicone material.

14. The method of claim 9, wherein the sheet of fabric is configured to grip the heated underbody support.

15. The method of claim 9, wherein the heated underbody support is anchored to the surgical table by a Velcro attachment between an upper surface of the surgical table and a lower surface of the heated underbody support.

16. A heated patient securing system for use during surgery in which a surgical table is titled into a head-down Trendelenburg position, comprising:
- a heated underbody support configured to support a patient on the surgical table, wherein the heated underbody support comprises a heating element, an upper shell, and a lower shell, wherein the upper shell and the lower shell encase the heating element;
- a strap attachment between a side of the surgical table and the heated underbody support for coupling the heated underbody support to the surgical table;
- a sheet of fabric configured to be positioned on an upper surface of the heated underbody support between the upper surface of the heated underbody support and the patient, the sheet of fabric comprising an upper surface and a lower surface;
- the sheet of fabric being at least partially coated on both the upper surface and the lower surface thereof with three-dimensional friction enhancing elements, the three-dimensional friction enhancing elements comprising a three-dimensional raised pattern or three-dimensional raised dots, the three-dimensional friction enhancing elements comprising plastic or rubber, the three-dimensional friction enhancing elements preventing the patient from inadvertently slipping off of the heated underbody support;
- the three-dimensional friction enhancing elements being oriented such that the three-dimensional raised pattern or three-dimensional raised dots on the lower surface of the sheet of fabric are configured to grip the upper surface of the heated underbody support and the three-dimensional raised pattern or three-dimensional raised dots on the upper surface of the sheet of fabric are configured to grip a back of the patient;
- wherein the sheet of fabric grips the heated underbody support and is configured to prevent sliding of the patient relative to the surgical table, the heated underbody support being configured to be coupled to the surgical table such that the sheet of fabric is indirectly attached to the surgical table.

17. The heated patient securing system of claim 16, wherein the sheet of fabric partially coated with the three-dimensional friction enhancing elements is placed on the upper surface of the heated underbody support such that the sheet of fabric is configured to grip the heated underbody support.

18. The heated patient securing system of claim 16, wherein the three-dimensional friction enhancing elements form a raised pattern or raised dots on both the upper and lower surfaces of the sheet of fabric such that the partially coated sheet of fabric is uncoated on both the upper and lower surfaces thereof in areas between the raised pattern or raised dots.

19. A heated patient securing system for use during surgery, comprising:
- an underbody support, wherein the underbody support is heated, wherein the underbody support comprises a heating element, an upper shell, and a lower shell, wherein the upper shell and the lower shell encase the heating element;
- a draw sheet configured to be positioned over an upper surface of the underbody support for lifting a patient;
- the draw sheet includes friction enhancing elements applied to at least a portion of the draw sheet;
- the three-dimensional friction enhancing elements comprising a three-dimensional raised pattern or three-dimensional raised dots, the three-dimensional friction enhancing elements comprising plastic or rubber;
- the three-dimensional friction enhancing elements being configured to reduce sliding of the patient relative to the underbody support.

20. The heated patient securing system of claim 19, wherein the draw sheet is partially coated on both the upper surface and the lower surface thereof with the three-dimensional friction enhancing elements.

21. The heated patient securing system of claim 20, wherein the three-dimensional friction enhancing elements are configured to grip both the underbody support and the patient to prevent the patient from inadvertently slipping off of the underbody support.

22. The heated patient securing system of claim 21, wherein at least some of the friction enhancing elements are located on a portion of the draw sheet configured to contact the patient.

* * * * *

UNITED STATES PATENT AND TRADEMARK OFFICE
CERTIFICATE OF CORRECTION

PATENT NO. : 10,575,784 B2  
APPLICATION NO. : 16/209020  
DATED : March 3, 2020  
INVENTOR(S) : Scott D. Augustine et al.

Page 1 of 1

It is certified that error appears in the above-identified patent and that said Letters Patent is hereby corrected as shown below:

In the Claims

Claim 16, Column 31, Line 12, Delete "titled" and insert -- tilted --

Signed and Sealed this  
Fifth Day of May, 2020

Andrei Iancu  
*Director of the United States Patent and Trademark Office*